United States Patent [19]

Takeuchi et al.

[11] Patent Number: 5,786,535

[45] Date of Patent: Jul. 28, 1998

[54] FLAW DETECTION APPARATUS EMPLOYING TIRE PROBES HAVING ULTRASONIC OSCILLATORS MOUNTED THEREIN

[75] Inventors: Shinichi Takeuchi; Ryo Ishiyama; Yutaka Kashiwase; Kinuko Kato; Ryohei Motegi, all of Tokyo, Japan

[73] Assignee: Tokimec Inc., Tokyo, Japan

[21] Appl. No.: 749,844

[22] Filed: Nov. 15, 1996

Related U.S. Application Data

[62] Division of Ser. No. 337,462, Nov. 8, 1994, Pat. No. 5,602,336.

[30] Foreign Application Priority Data

Nov. 12, 1993 [JP] Japan ................................. 5-282918

[51] Int. Cl.$^6$ .......................... G01N 29/06; G01N 29/10; G01N 29/26
[52] U.S. Cl. ........................ 73/624; 73/622; 73/619; 73/639; 73/641
[58] Field of Search ........................... 73/639, 618, 619, 73/620, 622, 624, 627, 632, 633, 635, 641, 644, 597, 625, 626

[56] References Cited

U.S. PATENT DOCUMENTS

| 2,937,522 | 5/1960 | McGaughey | 73/633 |
| 4,165,648 | 8/1979 | Pagano | 73/625 |
| 4,174,636 | 11/1979 | Pagano | 73/636 |
| 4,689,995 | 9/1987 | Turbe | 73/636 |
| 5,404,755 | 4/1995 | Olson et al. | 73/639 |

Primary Examiner—Hezron E. Williams
Assistant Examiner—Rose M. Miller
Attorney, Agent, or Firm—Wenderoth, Lind & Ponack

[57] ABSTRACT

An apparatus for detecting flaws using supersonic waves measures a thickness of a test object or a position of a cavity inside the test object by employing a pair of ultrasonic probes. By, changing a relative position of one ultrasonic probe to that of the other ultrasonic probe, a plurality of waveform data of ultrasonic reception signals is acquired. Each of the acquired waveform data is added together. Because a surface wave component of each waveform data has a shifted phase due to a difference in arrival times, a level of the surface wave component is offset and thus minimized through addition of the waveform data.

1 Claim, 21 Drawing Sheets

L+0.0λSAW

L+0.2λSAW

L+0.4λSAW

L+0.6λSAW

L+0.8λSAW

ADDED WAVEFORM

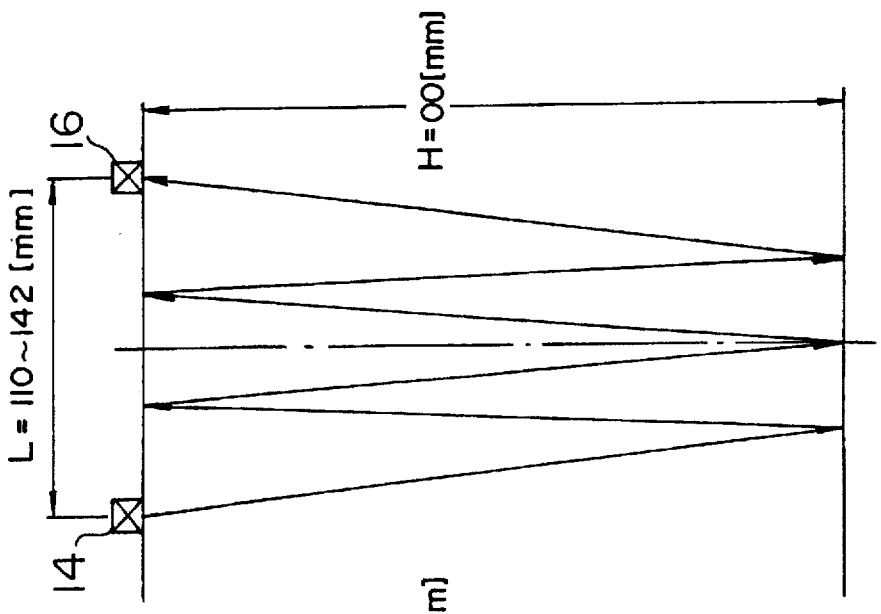
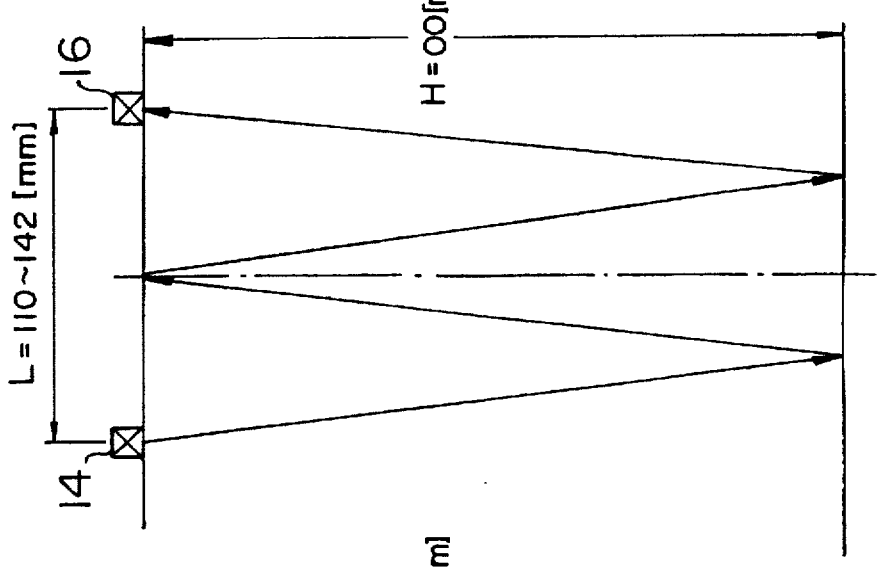
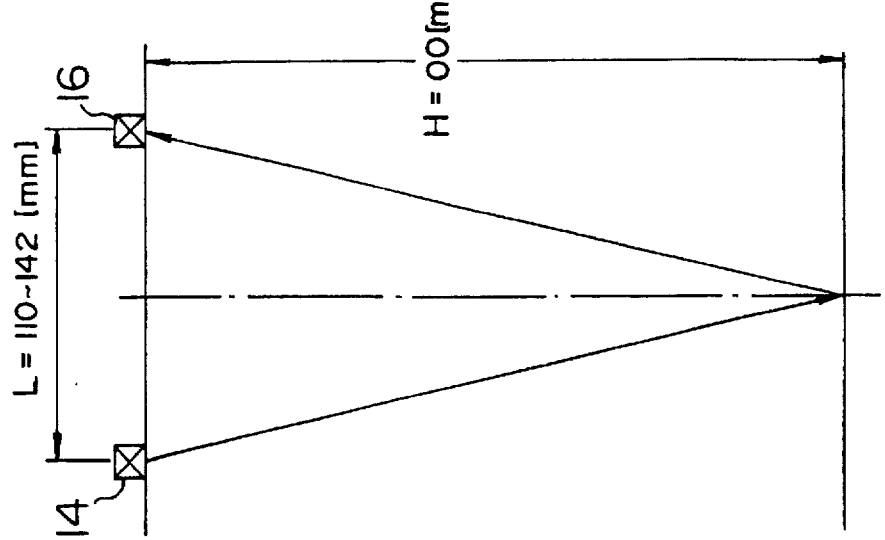

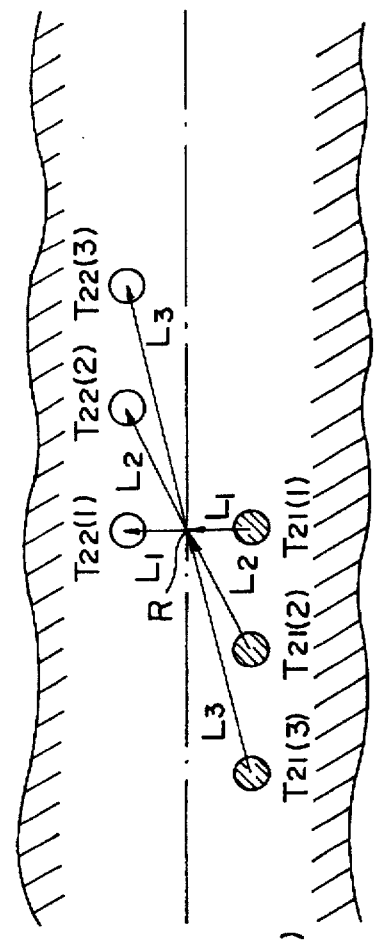
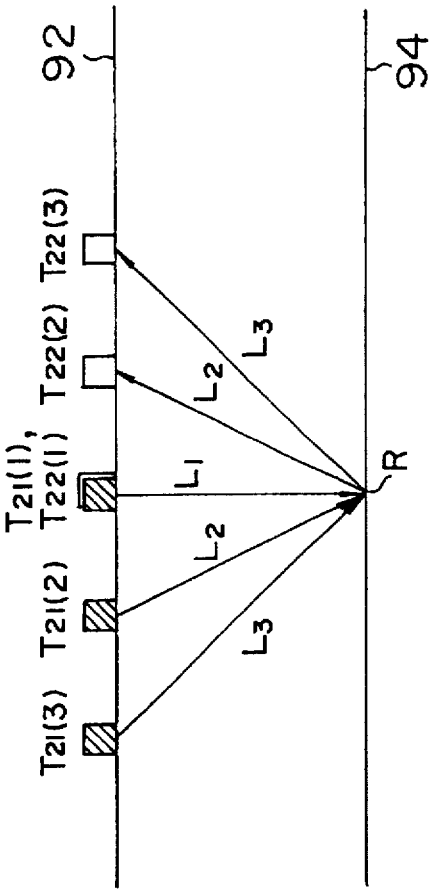
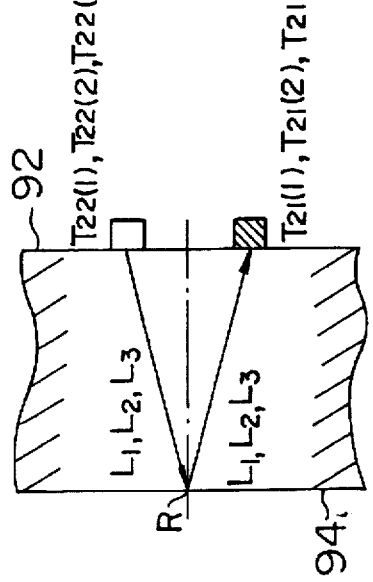
FIG. 11A
FIG. 11B
FIG. 11C

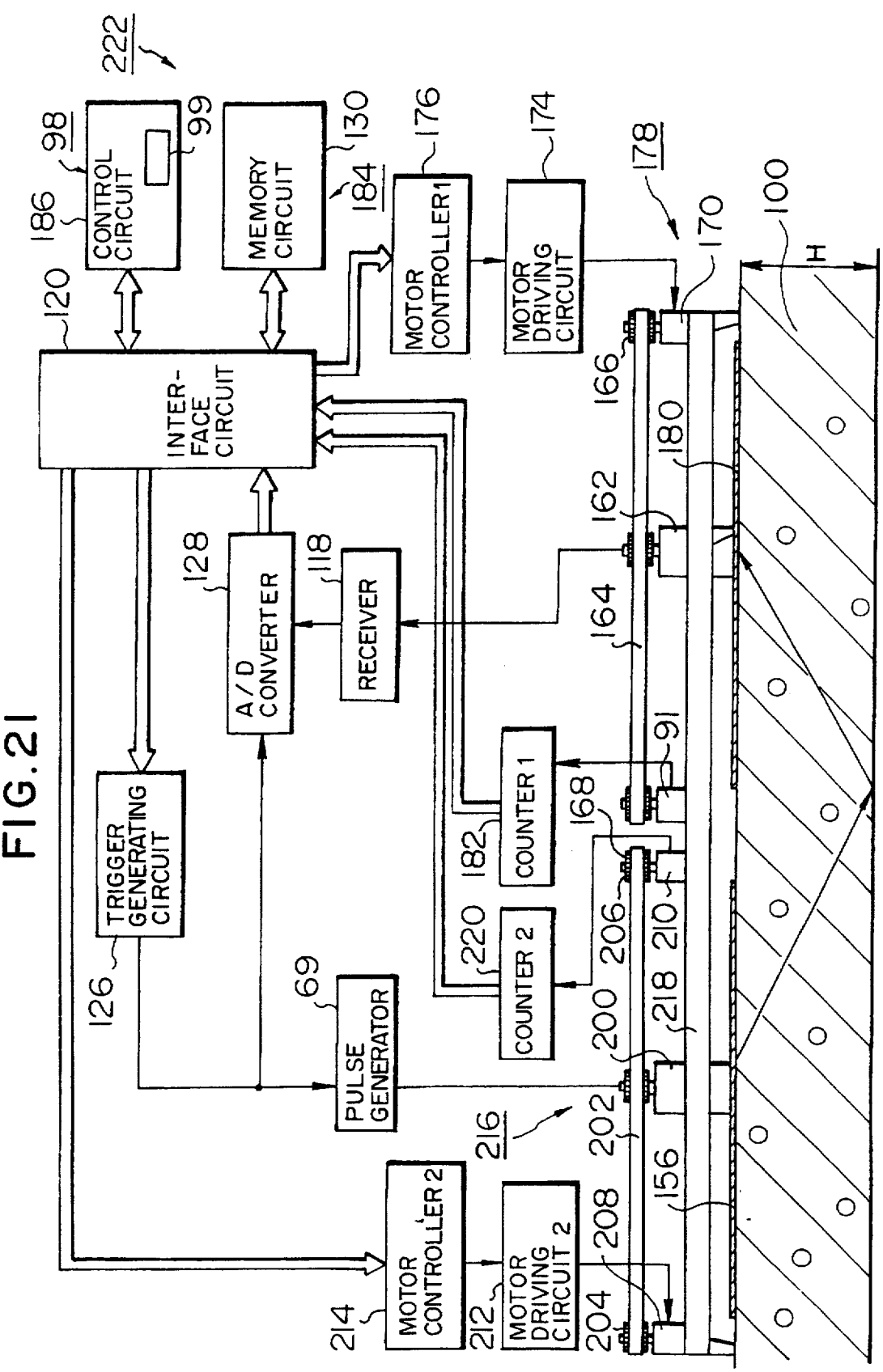

FLAW DETECTION APPARATUS EMPLOYING TIRE PROBES HAVING ULTRASONIC OSCILLATORS MOUNTED THEREIN

This application is a Divisional of application Ser. No. 08/337,462, filed Nov. 8, 1994 and now U.S. Pat. No. 5,602,336.

BACKGROUND OF THE INVENTION

1. Field of the Invention

The present invention relates to an apparatus for detecting flaws using supersonic waves to perform non-destructive tests of civil engineering and building structures such as asphalt paved roads, concrete paved roads and external walls of tunnels using a low frequency ultrasonic wave, and more particularly, to an apparatus for detecting flaws using supersonic waves to accurately measure defect positions and thicknesses without interference by a surface wave.

2. Description of the Related Art

Heretofore, apparatuses for detecting flaws using supersonic waves, used for non-destructive tests of civil engineering and building structures and the like, infer internal states of whether defects such as cavities and the like exist by observing ultrasonic reception waveforms with an oscilloscope through disposing ultrasonic probes for transmission and for reception in a predetermined distance with water, glycerin, or the like lying between them and a test object. However, since a spot non-destructive test cannot detect internal defects sufficiently and works for changing a measuring point are complicated, the inventor et al., of the present invention have proposed an apparatus for detecting flaws using supersonic waves, i.e., the type of the system shown in FIG. 1 (Japanese Patent Laid-Open No. Hei 5-080,035 published on Mar. 30 in 1994) that performs a non-destructive test of internal states of a civil engineering and building structure using a tire probe having built-in ultrasonic probes for transmission and for reception.

In FIG. 1, a tire probe 302 is provided in free rotation inside a main frame of an apparatus 300. The tire probe 302 is equipped with a rubber tire 304 made of hard urethane rubber, and a Gel sheet 306 outside the tire. As the Gel sheet 306, high polymer Gel of elastic can be used as disclosed in, for example, Japanese Patent Laid-Open No. Hei 1-304,102. Both wheels of the rubber tires 304 are provided with a pivot 308 which is mounted on a probe mounting axle 312 fixed through bearings 310 in free rotation in the main frame of the apparatus 300. In addition, an oil seal 314 is provided inside the bearings 310 so as to prevent outside leakage of medium liquid such as water and the like, filled in the rubber tire 304. A mounting frame 316 is attached to the center of the probe mounting axle 312, a ultrasonic probe for transmission 318 and a ultrasonic probe for reception 320 are mounted on the bottom of the mounting frame 316. From the ultrasonic probe for transmission 318 and the ultrasonic probe for reception 320, signal lines 322 and 324 are wired and connected to a transmission circuit and a receiving circuit respectively, both of which are not shown. Further, auxiliary wheels 326 are provided in the main frame of the apparatus 300 so that stable running of the main frame of the apparatus 300 can be attained.

According to an apparatus for detecting flaws using supersonic waves using such a tire probe, by making the tire probe 302 run on a test object, cross-sectional layer images showing a running distance in a horizontal axis are displayed on a CRT monitor so that a internal defect such as an cavity can be certainly found. However, in an apparatus for detecting flaws using supersonic waves using a tire probe, a surface wave propagated near a surface of the test object interferes with reflective waves from acoustic discontinuous points inside the test object or from the bottom of the test object. Consequently, this lead to the problem that rise time and existing time of the reflection waves in a reception waveform become unclear, this causes large errors in precision of a non-destructive test, for example, identification of defect positions inside the test object and thickness measurements, and this causes impossible measurements.

For example, as shown in FIG. 2, when a non-destructive test is performed through rotationally moving the tire probe 302 on a test surface 330 of the test object 328 will be described. Ultrasonic waves transmitted from the ultrasonic probe 318 for transmission built in the tire probe 302 pass through a path of water of medium liquid (1), and a propagation path of longitudinal waves in an asphalt paved road (4) and (5), they arrive at the ultrasonic probe for reception 320 through a path in a tire (3), and the ultrasonic probe for reception obtains longitudinal wave reflection echoes including information of thickness H of the test object 328. At the same time, the ultrasonic waves transferred from the ultrasonic probe 318 embedded in the tire probe 302 arrive at the ultrasonic probe for reception 320 through the path in the water inside the tire (1), the propagation path of the surface waves on the test object 328 (2) and the path in the water inside the tire (3). In this case, these waves do not include thickness information of the asphalt paved road, and interfere with the longitudinal wave reflection echo as surface waves becoming disturbing waves upon thickness measurement and the like. Consequently, a reception waveform becomes as shown in FIG. 3, the rise position of the bottom echo becomes unclear, and hence, these waves become obstacles to thickness measurement of the test object.

Besides the tire probe, these conventional problems also arise at apparatuses for detecting flaws using supersonic waves adopting the type of a ultrasonic probe that directly contacts a test object with an acoustic contact medium.

SUMMARY OF THE INVENTION

According to the present invention, an apparatus for detecting flaws using supersonic waves and a tire probe, both of which make measurements of defect positions and thickness in high precision through removing influences of interference by surface waves, are provided. In an apparatus for detecting flaws using supersonic waves to measure the thickness of a test object, a cavity position inside the test object or the like, using a pair of ultrasonic probes, an apparatus according to the present invention for detecting flaws using supersonic waves changes a position of one ultrasonic probe relative to that of the other ultrasonic probe, acquires a plurality of ultrasonic reception waveform data at a plurality of positions during the change, and adds these waveform data per corresponding time.

In addition, an apparatus according to the present invention for detecting flaws using supersonic waves uses a tire probe as an ultrasonic probe, which comprises a rotational driving means for independently rotationally driving a pair of tires each mounting an ultrasonic oscillator.

An apparatus according to the present invention for detecting flaws using supersonic waves adopting a tire probe controls to fix one of a pair of tires of a tire probe at a definite position on the test object during a definite period of measurement by a control means, and to rotationally drive the other tire. During the subsequently definite period, this controls to fix the tire having rotationally driven during the previously definite period at a definite position, and to rotationally drive the other tire which was fixed during the previously definite period. A reception data acquisition memory means acquires and stores waveforms of ultrasonic reception signals at each of a plurality of predetermined positions during each definite period. Finally, an adding means adds each waveform, acquired with the reception data acquisition memory means, per corresponding time.

Further, after initializing with a control means so that a distance between both of tires becomes a predetermined value through locating a tire probe at optionally designated positions on a test object, another apparatus according to the present invention for detecting flaws using supersonic waves adopting the tire probe controls, on the basis of the initially set positions to rotationally drive a pair of tires on a test object in order that the pair of tires run in definite but opposite directions for the same distance. In this case, a reception data acquisition memory means acquires and stores waveforms of ultrasonic reception signals at each of a plurality of predetermined positions, and an adding means adds each waveform, acquired with the reception data acquisition memory means, per corresponding time.

Furthermore, still another apparatus according to the present invention for detecting flaws using supersonic waves adopting a tire probe, as a tire probe, comprises a pair of tires which mount ultrasonic oscillators transmitting or receiving ultrasonic waves and are disposed on a line along the longitudinal direction of a frame on the frame, and a driving means for moving the frame on the test object through rotationally driving one tire of the tire probe and for relatively moving the pair of tires on the frame through rotationally driving the other tire. In this case, the control means controls to rotationally drive one tire of the tire probe, to move the tire probe on the test object, and simultaneously, to rotationally driving the other tire so as to change the distance to the former tire. A reception data acquisition memory means acquires and stores waveform data of ultrasonic reception signals at each of a plurality of predetermined positions during rotational driving of a pair of tires by the control means. And, an adding means adds each waveform data, acquired with the reception data acquisition memory means, per corresponding time.

Further, a further apparatus according to the present invention for detecting flaws using supersonic waves uses an array type of ultrasonic oscillators composed of a plurality of element oscillators for transmission and a plurality of element oscillators for reception, both of which are located through an acoustic connection medium on a test object. Driving of each element oscillator is switched by a switching means, and the means is controlled switching by a switching control means. Furthermore, A reception data acquisition memory means acquires and stores waveform data of ultrasonic reception signals at each of a plurality of positions of the array type of ultrasonic oscillators. And an adding means adds each waveform data, acquired with the reception data acquisition memory means, per corresponding time.

Assuming that the number of the element oscillators is N, the switching means in this case drives, as an oscillator for transmission, n pieces of element oscillators from the {(N/2)−n+1}th element oscillator to the (N/2)th one on the basis of its center, drives, as an oscillator for reception, n pieces of element oscillators from the {(N/2)+1}th element oscillator to the {(N/2)+n}th one, and controls to switch each element in a mirror image on the basis of its center in shifting one-by-one with electronic scanning.

Further, a still further apparatus according to the present invention for detecting flaws using supersonic waves can be composed of a single ultrasonic oscillator having a predetermined area instead of a plurality of element oscillators for transmission and residual element oscillators as the oscillator for reception.

Although such an apparatus for detecting flaws using supersonic waves and a tire probe acquire waveforms of ultrasonic reception signals at each of a plurality of predetermined positions through changing a position of one ultrasonic probe or a tire probe relative to that of the other ultrasonic probe or tire probe, the distance between both ultrasonic probes or tire probes is different at each time acquired reception waveform. Therefore, arrival times of surface waves, and arrival times of target echoes and bottom echoes at each time acquired reception waveform are also different. The arrival time of a surface wave changes approximately proportionally to the distance between ultrasonic probes or tires for transmission and reception. On the other hand, although arrival times of a target echo and a bottom echo changes with the distance between both ultrasonic probes or both tires, it is not proportional to the distance, and variance of the arrival time of a target echo in depth equal to or more than a definite value or a bottom echo in thickness equal to or more than a definite value is very small even if the distance between both ultrasonic probes or both tires changes. Therefore, changing a position of one ultrasonic probe or one tire probe relative to that of the other ultrasonic probe or the other tire probe, acquiring reception waveforms at a plurality of predetermined positions, and adding these waveforms per corresponding time, a level of a surface wave component becomes low by a phase canceling effect because of different arrival times. However, since the arrival time of the target echo or the bottom echo scarcely change, this echo is emphasized and its level increases. Consequently, measurement precision of defect positions and thicknesses can be greatly improved. In addition, in case, after initializing so that a distance between a pair of ultrasonic probes or tire probes becomes a predetermined value through locating them at optionally designated positions on a test object, an apparatus controls on the basis of the initially set positions so as to make them over the definite but opposite directions in same distance, cross-sectional layer images of the test object cannot be obtained, but thicknesses of a specific position of the test object can be measured more accurately.

The above and other objects, features, and advantages of the present invention will become more apparent from the following detailed description with reference to the drawings.

BRIEF DESCRIPTION OF THE DRAWINGS

FIGS. 9A to 9C are model diagrams of propagation paths and propagation time of bottom reflection echoes;

FIGS. 11A to 11C are explanatory diagrams of ultrasonic measurement lines inside a test object.

FIG. 21 is a schematic structure and circuit block diagram of the eighth embodiment of the present invention.

DETAILED DESCRIPTION OF THE PREFERRED EMBODIMENTS

Figure 4:
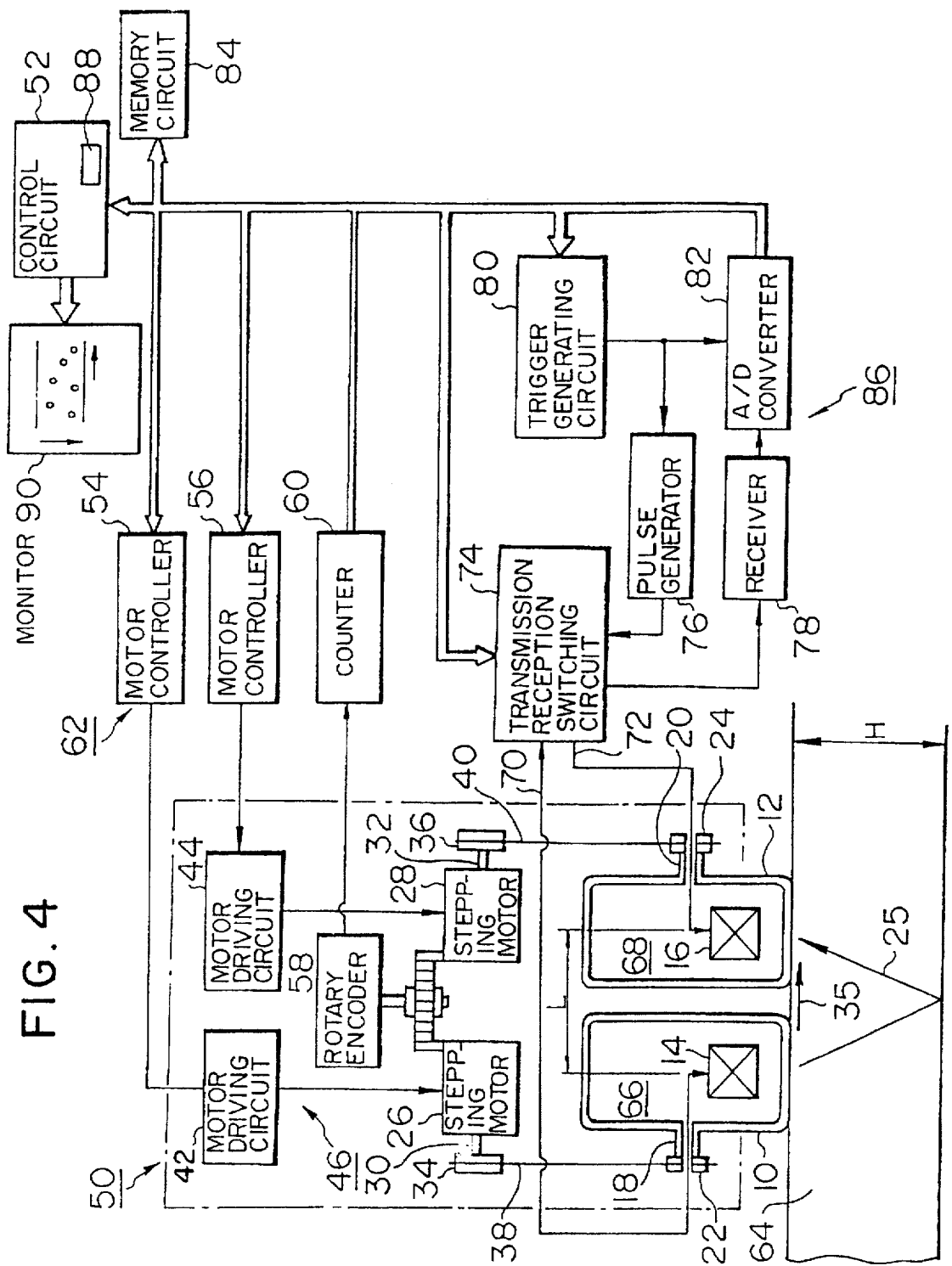
FIG. 4 is a schematic structure and circuit block diagram of the first embodiment of the present invention.

FIG. 4 to FIGS. 9A-9C show the first embodiment of the present invention. In FIG. 4, ultrasonic oscillators 14 and 16 are embedded in tires 10 and 12. In the tire 10 and 12, axles 18 and 20 are provided respectively, and in the axles 18 and 20, driving gears 22 and 24 are provided respectively. Stepping motors 26 and 28 have axles 30 and 32, and in the axles 30 and 32, driving gears 34 and 36 are provided. Between the driving gears 34 and 36 of the stepping motors 26 and 28 and the driving gears 22 and 24 of the tires 10 and 12, driving belts 38 and 40 are wrapped respectively. The stepping motors 26 and 28 are rotationally driven with motor driving circuits 42 and 44 respectively. These motor driving circuits 42 and 44, and stepping motors 26 and 28 compose the driving means 46 for rotationally driving the tires 10 and 12.

Figure 5:
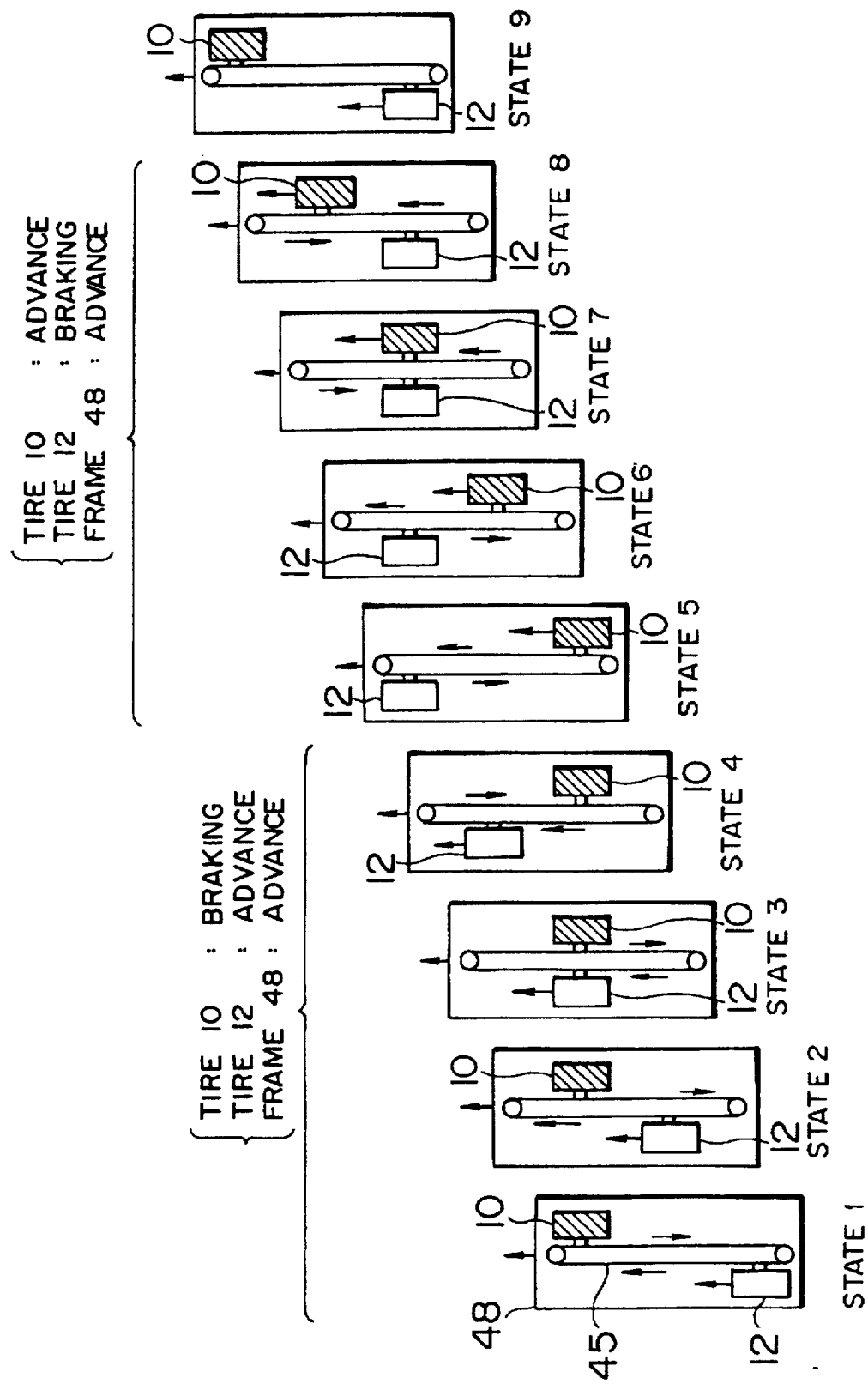
FIG. 5 is an explanatory diagram showing movement of a tire probe.

In addition, as shown in FIG. 5, the tires 10 and 12 are connected with a timing belt 45, and can move on a frame 48 with the driving means 46. The driving means 46, tires 10 and 12, ultrasonic oscillators 14 and 16, timing belt 45, and frame 48, as a whole, compose a tire probe 50.

The tires 10 and 12 are rotated with driving force of the stepping motor 26 and 28. Since the stepping motor 26 and 28 can rotate or stop through motor controllers 54 and 56, and the motor driving circuits 42 and 44 with commands of a control circuit 52 composed of a computer, they can brake and stop the tires 10 and 12 at designated positions, and rotationally move the tires to designated positions with commands from the control circuit 52. Further, the control circuit 52 can recognize the positions of the tires 10 and 12 on the frame 48 with a rotary encoder 58 and a counter 60. Thus, the counter 60 counts outputs of the rotary encoder 58, and outputs the count to the control circuit 52. The control circuit 52 recognizes the positions of the tires 10 and 12 on the frame 48 on the basis of the output of the counter 60, and controls to brake, stop and rotationally drive the tires 10 and 12 with the motor controller 54 and 56, motor driving circuits 42 and 44, and stepping motors 26 and 28. Therefore, the rotary encoder 58, counter 60, motor controller 54 and 56, and the control circuit 52 compose a control means 62 for controlling the driving means 46. In the control circuit 52, programs to control the driving means 46 are embedded so that the tires 10 and 12, and frame 48 operate on the test object 64 as states 1 to 9 shown in FIG. 5.

Subsequently, movement of the tires 10 and 12, and frame 48 will be described on the basis of FIG. 5. At first, if the tires 10 and 12, and frame 48 are set at the initial state with a command from the control circuit 52, the tires 10 and 12 are set at positioning relations of the state 1 in FIG. 5 on the frame 48. Subsequently, if the tire 10 is subjected to braking and stopping with a command from the control circuit 52, the tire 10 is locked at the current position on the test object 64 with the stepping motor 26. During the braking and stopping of the tire 10 the tire 12 is rotationally moved with a command from the control circuit 52, and then, positioning relations of the tires 10 and 12, and frame 48 change from the state 1 to the state 5. In this time, since the tires 10 and 12 are fixed to the timing belt 45 on the frame 48, and the tire 10 is locked at one point on the test object 64, the frame 48 advances at a half speed of the tire 12 if the tire 12 advances.

When the state of the tire probe 50 arrives in the state 5, the tire 12 is locked after braking and stopping on the basis of a command from the control circuit 52. Further, rotationally moving the tire 10 with a command from the control circuit 52, positioning relations of the tires 10 and 12, and frame 48 change from the state 5 to the state 9. The frame 48 also advances at a half speed of the tire 10. Repeating such operations of the state 1–5 and state 5–9 in FIG. 5 alternatively, the tire probe 50 advances on the test object 64 at a half advancing speed of the tire 10 or 12.

Referring to FIG. 4 again, a ultrasonic oscillator 14 is disposed downward in the tire 10, and the tire 10 is filled with water 66, for example, as a liquid medium. In addition, an ultrasonic oscillator 16 is disposed downward in the tire 12, and the ire is filled with water 68, for example, as a liquid medium, as the ultrasonic oscillators 14 and 16 are connected to a pulse generator 76 for a pulse generation circuit or a receiver 78 for ultrasonic wave reception circuit through signal lines 70 and 72, and a transmission/reception switching circuit 74. The transmission/reception switching circuit 74 switches to use either of the ultrasonic oscillator 14 or ultrasonic oscillator 16 for transmission, and to use the other for reception with a command from the control circuit 52.

Figure 1:
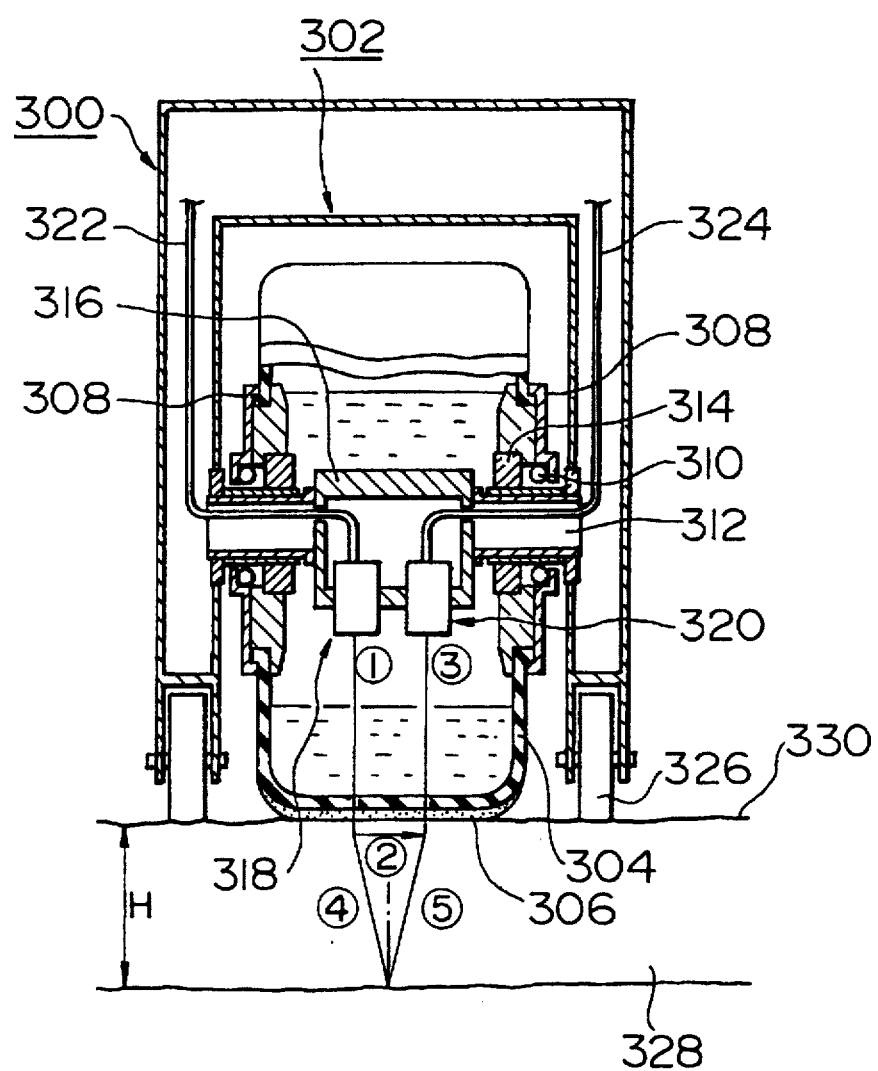
FIG. 1 is a cross-sectional view showing a conventional tire probe.
Figure 2:
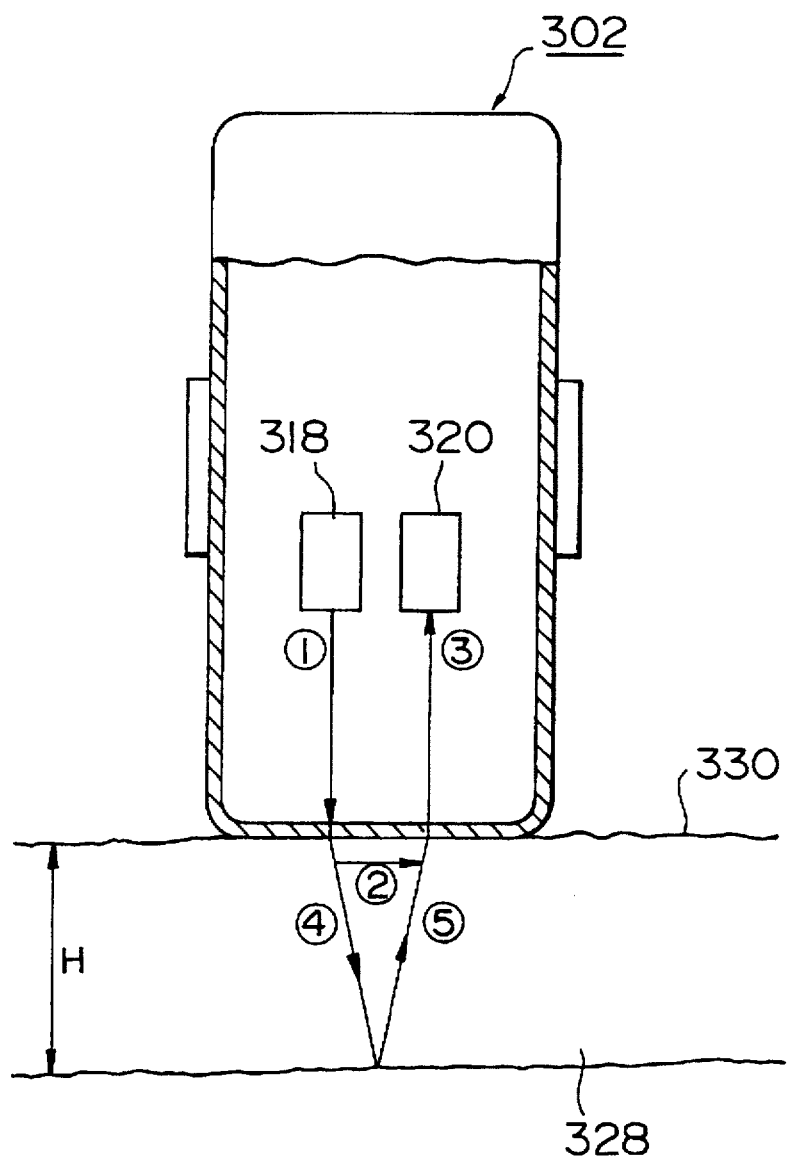
FIG. 2 is an explanatory diagram showing a propagation state of surface waves and longitudinal waves.
Figure 3:
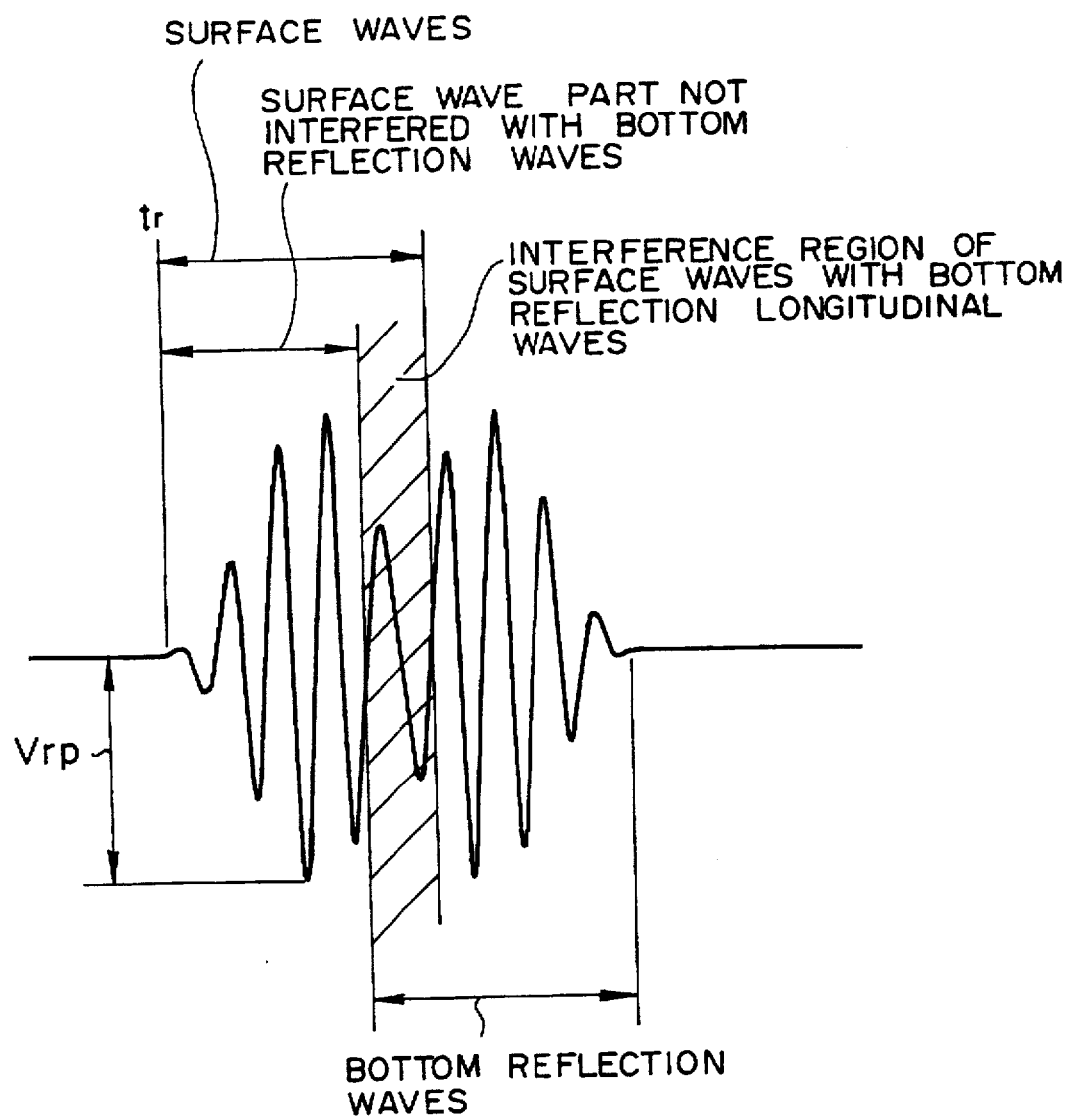
FIG. 3 is an explanatory diagram showing an interference region of surface waves.

The pulse generator 76, on the basis of a trigger signal generated in a trigger generating circuit 80 with a command from the control circuit 52, drives the ultrasonic oscillator 14 or 16 designated for transmission with the transmission/ reception switching circuit 74. For example, if the ultrasonic oscillator 14 is designated for transmission and the ultrasonic oscillator 16 is designated for reception, the ultrasonic oscillator 14 generates pulsed ultrasonic waves, and propagates them inside the test object 64. The ultrasonic waves propagated inside the test object 64 arrive at the ultrasonic oscillator 16 through water 66 in the tire 10, and are received for conversion to electric signals. The received signals are amplified at a predetermined level with a receiver 78, after that, are converted to digital signals with an A/D converter 82 in the timing based on trigger signals generated in the trigger generating circuit 80, and are stored in a memory circuit 84. The reception data received in this time are waveform data interfered with surface waves, target echoes inside the test object, or bottom echoes, similarly to the reception waveform data in FIG. 3 that are obtained with a conventional tire probe. The transmission/reception switching circuit 74, pulse generator 74, trigger generating circuit 80, receiver 78, A/D converter 86, memory circuit 84, and control circuit 52, as a whole, compose a reception data acquisition memory means 86 for acquiring and storing ultrasonic reception waveform data from the ultrasonic oscillators 14 and 16 at a plurality of predetermined positions on the frame 48.

Still further, since the control circuit 52 has a function as an adding means 88, this adds each obtained reception waveform data per corresponding time. If the control circuit 52 adds each reception waveform data per corresponding time with the adding means 88, the level of the surface wave component is lowered because of a phase cancellation effect derived from their different arrival times, while the level of the target echoes or the bottom echoes increases due to emphasis by addition because of little change of their arrival times. Thus, waveform data composed of depressed surface waves, and emphasized target echoes or bottom echoes can be obtained.

Here, a monitor 90 is connected to the control circuit 52, and on the monitor 90, cross-sectional layer images of the test object 64 showing a running distance or position of the tire probe 50 in the horizontal axis and a depth in the vertical axis are displayed.

Subsequently, operations will be described. As shown in FIG. 4, it is defined that the center-to-center distance between the ultrasonic oscillators 14 and 16 is L, and thickness of the test object 64 is H. In addition, it is also defined that the sonic velocity of longitudinal waves 25 inside the test object 64 is $V_P$, and the sonic velocity of surface waves 35 is $V_{SAW}$. In this time, the arrival time $t_{SAW}$ of the surface wave component included in the reception waveform data is expressed as follows.

$$t_{SAW} = (L/V_{SAW}) + \tau \quad (1)$$

In addition, the arrival time $t_P$ of the bottom echo component derived from the longitudinal waves included in the reception waveform data is expressed as follows.

$$t_P = \{(L^2 + 4H^2)^{1/2}/V_P\} + \tau \quad (2)$$

Here, $\tau$ is the fixed delay time such as the fixed delay time arisen in the ultrasonic oscillators 14 and 16, fixed delay time in pulse generator 54 and receiver 55, propagation time inside water in the tires 10 and 12 and the like.

Then, if the center-to-center distance L between the ultrasonic oscillators 14 and 16 is changed, it is apparent from the expression (1) that the arrival time $t_{SAW}$ of the surface wave component changes almost proportionally to the distance L. On the other hand, it is apparent from the expression (2) that, if the center-to-center distance L between the ultrasonic oscillators 14 and 16 is changed, the arrival time $t_P$ of the bottom echo component does not change proportionally. For example, if the thickness of the test object 64 is sufficiently large in comparison with the center-to-center distance L between the ultrasonic oscillators 14 and 16, and satisfies the following formula:

$$H \gg (L/2) \quad (3)$$

the formula (2) can be expressed in the following formula:

$$t_P = \{(4H^2)^{1/2}/V_P\} + \tau = (2H/V_P) + \tau. \quad (4)$$

Therefore, in this case, if the center-to-center distance L between the ultrasonic oscillators 14 and 16 is changed, the arrival time $t_P$ of the bottom echo component does not change.

It can be easily inferred that, if the center-to-center distance L between the ultrasonic oscillators 14 and 16 is changed like this, the arrival time $t_{SAW}$ of the surface wave component changes almost proportionally to the distance L, but change of the arrival time $t_P$ of the bottom echo component is smaller than that of $t_{SAW}$. Thus, during a definite period of measurement, for example, fixing one tire 10 at a definite position on the test object 64, rotationally moving the other tire 12, acquiring the ultrasonic reception waveform data at a plurality of predetermined positions, and adding each of these waveform data per corresponding time, the arrival time $t_{SAW}$ of the surface wave component at each position of the tire 12 is different since the center-to-center distance L between the ultrasonic oscillators 14 and 16 is different at each position of the tire 12, and hence, the amplitude of the surface wave component after addition is depressed due to the phase canceling effect. On the other hand, since the arrival time $t_P$ of the bottom echo component hardly changes at each position of the tire 12, its amplitude increases with addition. Therefore, considering the surface wave component as a noise component, and the bottom echo component as a signal component, in the reception waveform after the addition processing, a S/N ratio is greatly improved, and hence, the bottom echo component in the reception waveform can be clarified.

Subsequently, relationship of tire movement to a degree of S/N ratio improvement, clarified in investigation with simulation will be described below.

Figure 6:
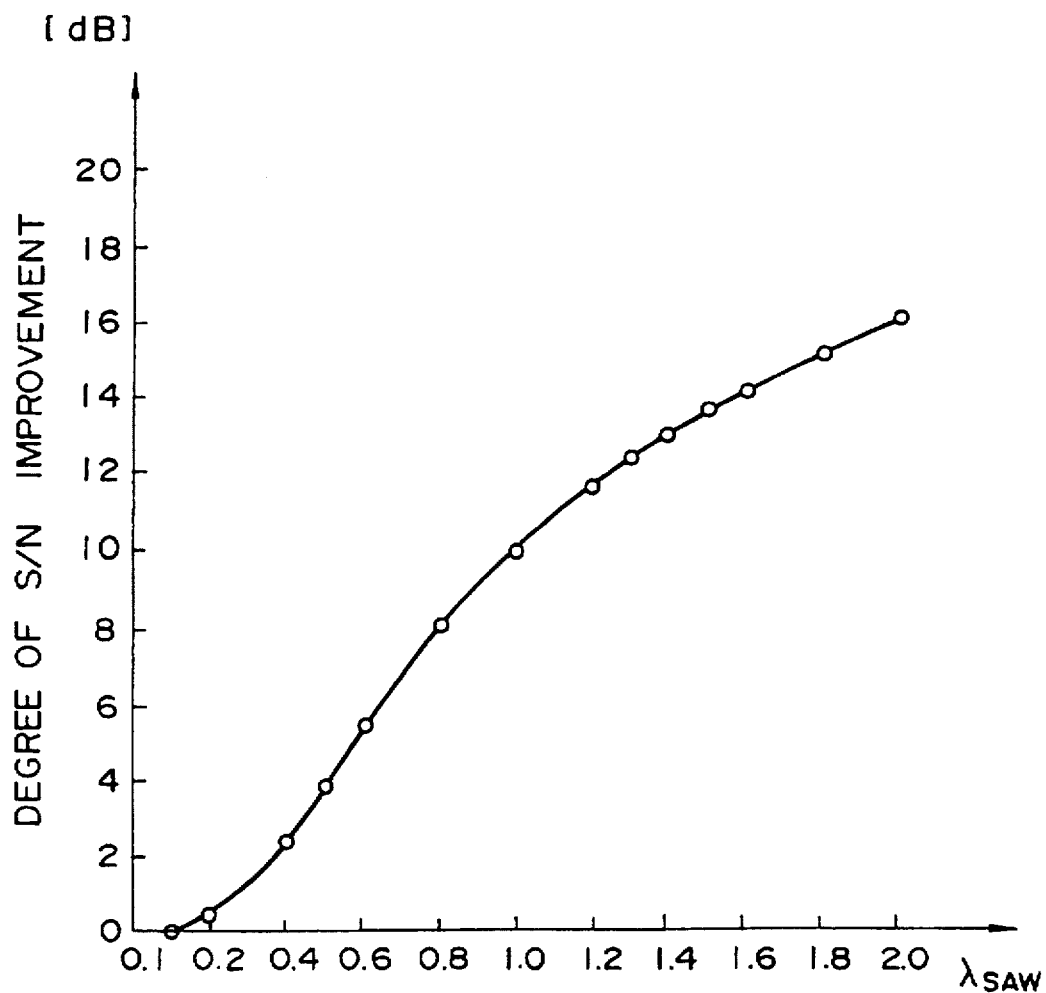
FIG. 6 is a graph showing relations of center-to-center distance between ultrasonic oscillators for transmission and reception to degree of S/N improvement.
Figure 7A:
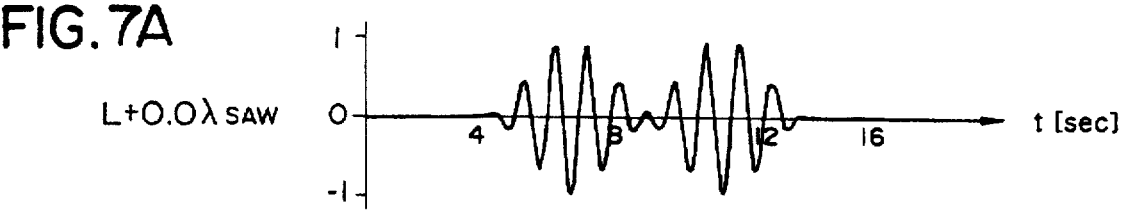
FIG. 7A to FIG. 7F show each reception waveform when a center-to-center distance is changed by 0.2 times of a wavelength $\lambda_{SAW}$ of a surface wave against a value L, and a waveform after addition of them.
Figure 7B:
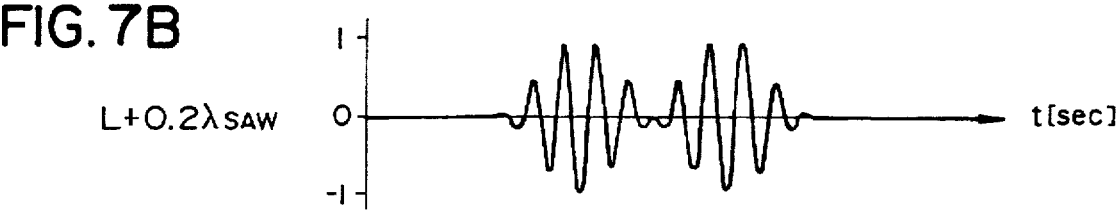
Figure 7C:
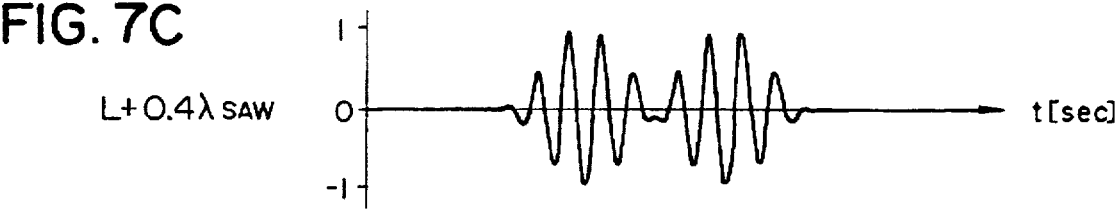
Figure 7D:
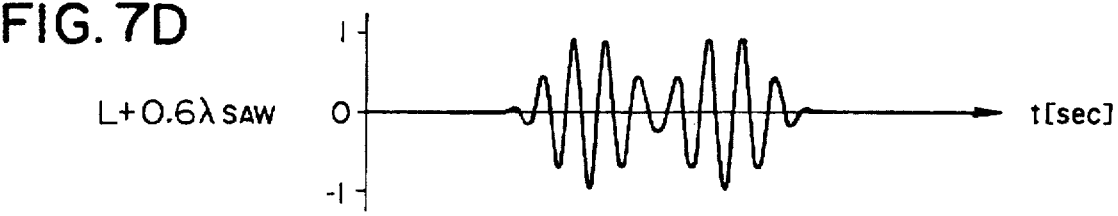
Figure 7E:
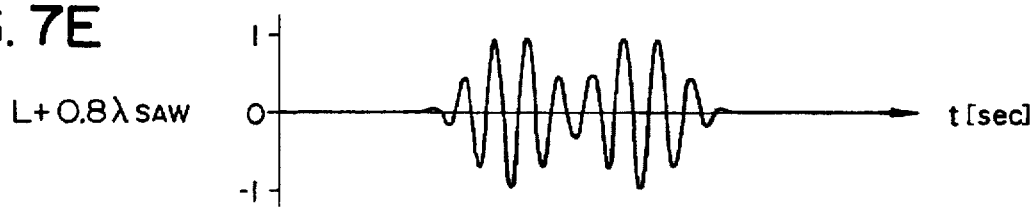
Figure 7F:
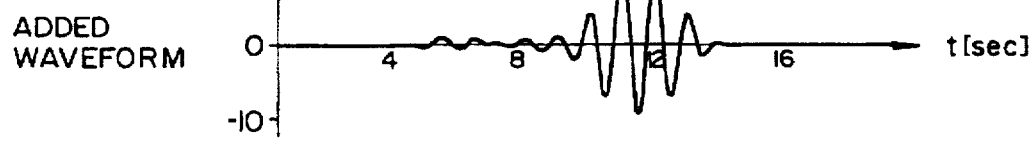

The graph in FIG. 6 shows the relationship of the changed range of the center-to-center distance L between the ultrasonic oscillators 14 and 16 when fixing a changing step of the center-to-center distance L between the ultrasonic oscillators 14 and 16 by 0.1 times of a wavelength $\lambda_{SAW}$ of a surface wave, to a degree of S/N ratio improvement. In this case, the changed step of the center-to-center distance L between the ultrasonic oscillators 14 and 16 is expressed in the wavelength $\lambda_{SAW}$ of a surface wave as a unit. Here, as an example, when the thickness measurement is performed as the test object 64 is a concrete block will be described. It is assumed that the sonic velocity of a longitudinal wave in the concrete block is 3800 m/s, and the propagation velocity of a surface wave is 2250 m/s. And, if the center frequency of the used ultrasonic pulses is assumed to be 70 kHz, the wavelength $\lambda_{SAW}$ of a surface wave on the concrete block at 70 kHz:

$$\lambda_{SAW} = V_{SAW}/f = 2250 \text{ [m/s]}/70 \text{ [kHz]} = 32 \text{ [mm]} \quad (5)$$

is obtained. Then, reception waveforms and an added waveform at each position in case of: using a tire probe 50 so that the minimum value of the center-to-center distance between transmission and reception ultrasonic oscillators 14 and 16 is $L_{min} = 110$ [mm]; braking and stopping the tire 10; rotationally moving the tire 12; increasing the center-to-center distance L between ultrasonic oscillators for transmission and reception 14 and 16 by a step of $0.1\lambda_{SAW} = 3.2$ [mm]; simulating to change the center-to-center distance L between ultrasonic oscillators for transmission and reception 14 and 16:

$$L = 110 \text{ [mm]} + \lambda_{SAW} \quad (6)$$
$$= 110 \text{ [mm]} + 32 \text{ [mm]}$$
$$= 142 \text{ [mm]},$$

are shown in FIGS. 7A to 7F. Here, FIG. 7A is in the case of L+0$\lambda_{SAW}$, FIG. 7B is in the case of L+0.2$_{SAW}$, FIG. 7C is in the case of L+0.4$\lambda_{SAW}$, FIG. 7D is in the case of L+0.6$\lambda_{SAW}$, FIG. 7E is in the case of L+0.8$\lambda_{SAW}$, and FIG. 7F is the added waveform of L+0$\lambda_{SAW}$ to L+1.0$\lambda_{SAW}$. Since each reception waveform in FIGS. 7A to 7E is a resultant waveform interfered with surface waves and bottom echoes, identification of the surface waves and bottom echoes is necessary. Then, the waveform in FIG. 7F is obtained through adding each reception waveform data per corresponding time. Although this waveform after addition has residual surface waves, the surface waves are depressed, the S/N ratio is improved, and the bottom echoes are clearly emphasized.

Figure 8:
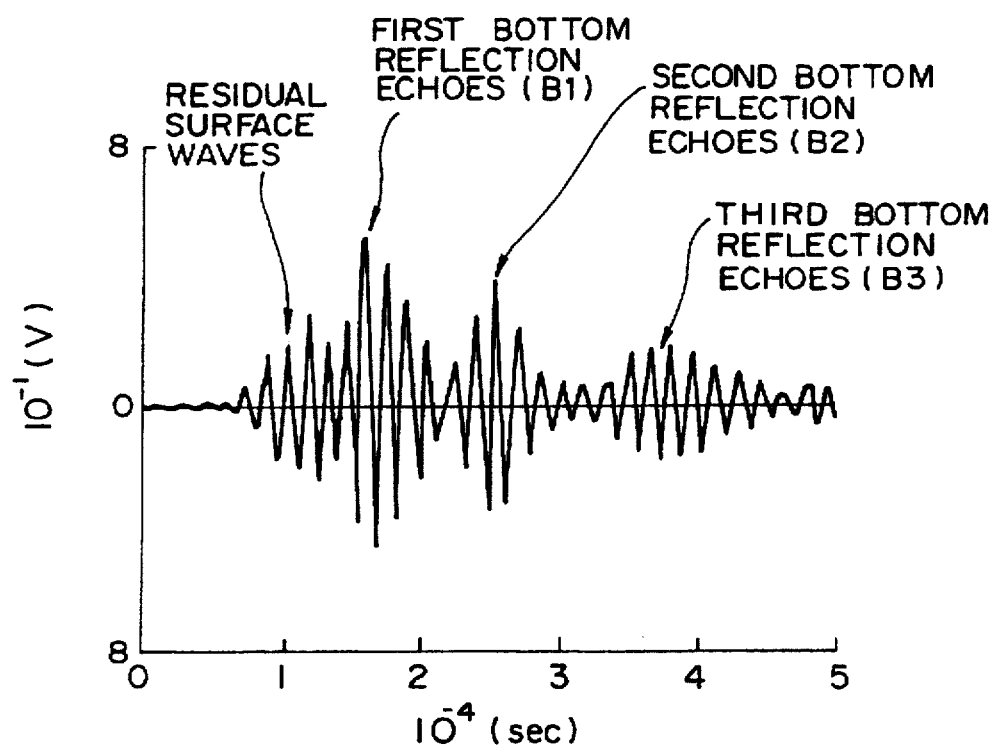
FIG. 8 is a reception waveform graph in actual measurement.
Figure 10A:
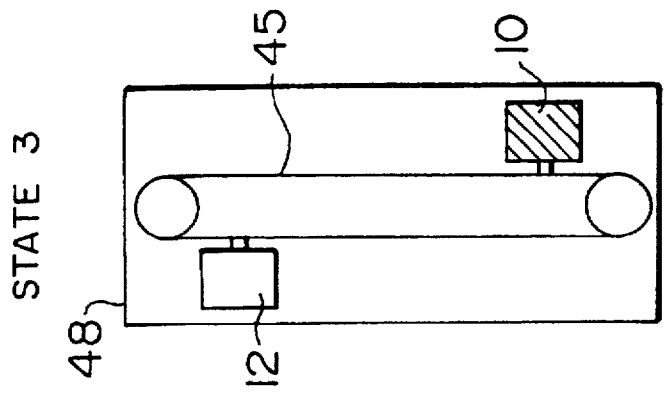
FIGS. 10A to 10C are explanatory diagrams of the second embodiment of the present invention.
Figure 10B:
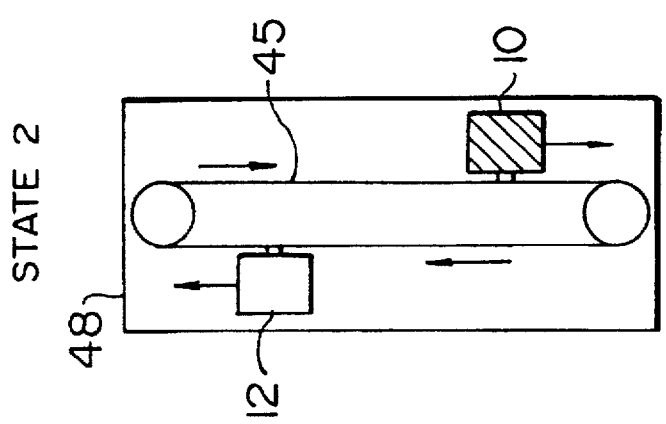
Figure 10C:
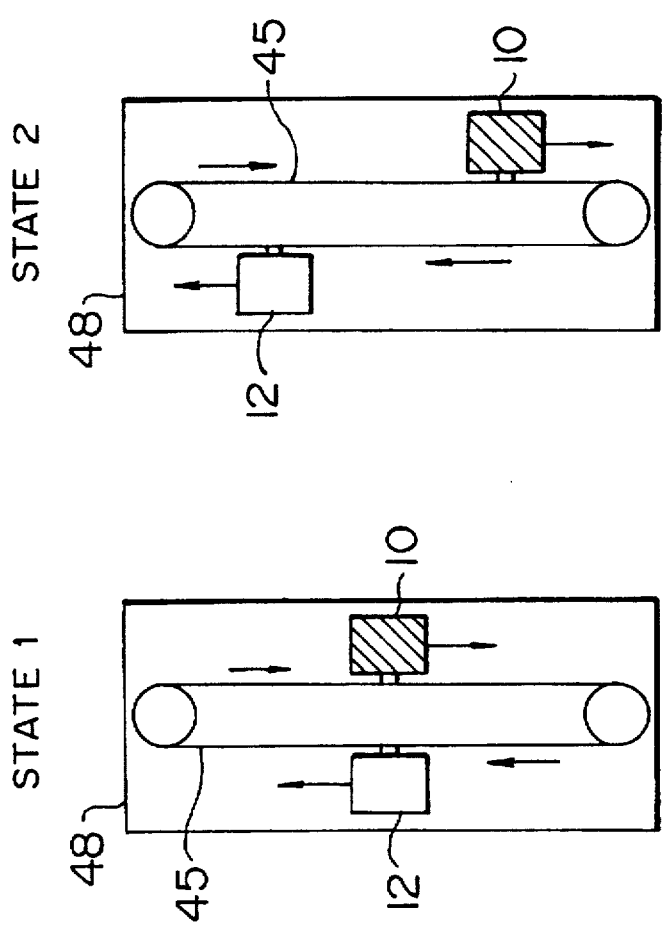

FIG. 8 is an added waveform graph obtained in actual measurement, the bottom echoes become clear, and the first bottom reflection echoes (B1), second bottom reflection echoes (B2), and third bottom reflection echoes (B3) can be easily recognized. Here, the first bottom reflection echoes (B1), second bottom reflection echoes (B2), and third bottom reflection echoes (B3) are, as in FIG. 9A, 9B and 9C, the echoes that ultrasonic pulses radiated from the ultrasonic oscillator for transmission 14 are reflected one, two, and three times respectively on the bottom of the concrete block of the test object 64 on the way to the ultrasonic oscillator for reception 16. The rise time of the first bottom reflection echoes, second bottom reflection echoes, and third bottom reflection echoes coincide well with the following calculated value of propagation time of each echo. Using the propagation paths of the first bottom reflection echoes, second bottom reflection echoes, and third bottom reflection echoes in FIGS. 9A, 9B, and 9C and the sonic velocity of a longitudinal wave, their propagation time $t_{P1}$, $t_{P2}$, and $t_{P3}$ calculated from the expression (2) become respectively as follows.

$t_{P1}$=120 to 122 μs $t_{P2}$=223 to 224 μs $t_{P3}$=327 to 328 μs

The reason why each propagation time has a range is correspondence to changing of the center-to-center distance L between the ultrasonic oscillators for transmission and reception 14 and 16 from 110 mm to 142 mm. Although, as for the first bottom reflection echoes in FIG. 8, their propagation time becomes slightly unclear due to interference with the residual surface waves, it can be surely considered as the first bottom reflection echoes because of the calculated values of the propagation time of the echoes, the calculated values attached to the model drawings in FIGS. 9A to 9C.

Then, if, in FIGS. 9A to 9C, the center-to-center distance L between the ultrasonic oscillators for transmission and reception 14 and 16, sonic velocity $V_P$ of longitudinal waves inside the test object 64, and fixed delay time are already known, calculation of the thickness H of the test object 64 becomes possible, since the unknown number becomes only the thickness H of the test object 64 if the propagation time $t_{P1}$, $t_{P2}$, and $t_{P3}$ are measured from the reception waveform.

Therefore, for example, if, in the transition process from the state 1 to the state 3 in movement of the tire probe 50 in FIG. 5, above-mentioned acquisition and addition process-ing of the reception waveforms are performed, it becomes possible to measure the average thickness of the test object, e.g., concrete in this section without interference of the surface waves. Similarly, if, in the transition process from the state 3 to the state 5, acquisition and addition processing of the reception waveforms are performed, it becomes possible to measure the average thickness of the test object in this section without interference of the surface waves. If, in each process of tire movement, the thickness of the test object 64, e.g., concrete is measured similarly to this, it becomes possible to measure the average thickness H of the test object along the running loci of the tire probe 50 without interference of the surface waves.

In addition, in case that a defect such as a cavity and the like exists inside the test object 64 under the running loci of the tire probe 50, its depth can be measured. Further, if the occurred positions of echoes are plotted on a monitor 90 showing a running distance or position of the tire probe 50 in the horizontal axis and a depth of the test object 64 in the vertical axis, a cross-sectional layer image of the test object 64 like that in FIG. 4 can be displayed. In this manner, measurement precision of inside defect position and thickness can be greatly improved.

Subsequently, the second embodiment of the present invention will be described, referring to FIGS. 10A to 10C, FIG. 11, and FIG. 12. In the first embodiment, a tire probe was described, the tire probe comprising a driving means 46 for rotationally driving independently a pair of tires 10 and 12 mounting an apparatus for detecting flaws using supersonic waves and ultrasonic oscillators 14 and 16, the apparatus for detecting flaws using supersonic waves comprising: a control means for controlling to fix the tire 10 of the tires at a definite position on the test object 64 during a definite period of measurement by a control means, and to rotationally drive the other tire 12, during the subsequently definite period, to fix the tire 12 having rotationally driven during the previously definite period at a definite position, and to rotationally drive the other tire 10 having fixed during the previously definite period; a reception data acquisition memory means 86 for acquiring and storing waveforms of ultrasonic reception signals at each of a plurality of predetermined positions during each definite period; further, an adding means 88 for adding each reception waveform data per corresponding time.

On the other hand, the second embodiment is characterized in a control means for controlling to initially set a distance between both of tires 10 and 12 at a predetermined value through locating tire probes at optionally designated positions on a test object, and to rotationally drive, on the basis of the initially set positions, a pair of tires 10 and 12 on a test object 64 in order that the pair of tires run in definite but opposite directions over the same distance. In addition, a reception data acquisition memory means 86 and an adding means 60 are the same as those in the first embodiment.

Using the same configuration as that of the apparatus according to the first embodiment for detecting flaws using supersonic waves, the apparatus according to the second embodiment for detecting flaws using supersonic waves can be realized through only changing steps of driving control of the tires 10 and 12. Then, operations of the tires 10 and 12, and frame 48 will be described on the basis of FIGS. 10A to 10C. At first, with a command from the control circuit 52, the tires 10 and 12, and frame 48 are initially set at optionally designated positions on the test object 64 as the state 1 in FIG. 10A so as that the distance between both of tires 10 and 12 becomes minimum. In this state 1, ultrasonic oscillators 14 or 16 mounted in the tires 10 or 12 is driven with a pulse generator 76 on the basis of trigger signals generated with a trigger generating circuit 80 by the control circuit 52, and radiates ultrasonic waves into the test object 64. Further, the ultrasonic waves arrive at the ultrasonic oscillator 16 or 14 mounted in the tire 12 or 10 from the test object 64, and are received. Subsequently, according to a command from the control circuit 52, the tires 10 and 12 are rotationally driven on the basis of the initial set positions in order that the tires are located in definite but opposite directions in the same distance on a test object, and have the positional relationship at the state 2 in FIG. 11B. At this time, similarly to the state 1 in FIG. 11A, the ultrasonic oscillator 14 or 16 mounted in the tires 10 or 12 is driven with a pulse generator 76 on the basis of trigger signals generated with a trigger generating circuit 80 by the control circuit 52, and radiates ultrasonic waves into the test object 64. Furthermore, the ultrasonic waves arrive at the ultrasonic oscillator 16 or 14 mounted in the tire 12 or 10 from the test object 64, and are received.

Still more, similarly to above, according to a command from the control circuit 52, the tires 10 and 12 are rotationally driven on the basis of the initial set positions in order that the tires are located in definite but opposite directions in the same distance on a test object, and have the positional relationship of the state 3 in FIG. 11C. At this time, similarly to the state 1 in FIG. 11A, the ultrasonic oscillator 14 or 16 mounted in the tires 10 or 12 is driven with a pulse generator 76 on the basis of trigger signals generated with a trigger generating circuit 80 by the control circuit 52, and radiates ultrasonic waves into the test object 64. Furthermore, the ultrasonic waves arrive at the ultrasonic oscillator 16 or 14 mounted in the tire 12 or 10 from the test object 64, and are received.

In this manner, after initializing with a control means so that a distance between both of tires becomes a predetermined value at optionally designated positions on a test object, this apparatus controls to rotationally drive, on the basis of the initial set positions, the pair of tires 10 and 12 in order that the tires are located in definite but opposite directions in the same distance on a test object, acquires and stores waveforms of ultrasonic reception signals at each of a plurality of predetermined positions in rotationally driving of the tires 10 and 12, and finally, adds each acquired waveform per corresponding time. Adding these waveforms per corresponding time, a level of a surface wave component becomes low by a phase canceling effect because of different arrival times. However, since the arrival times of the target echo or the bottom echo scarcely changes, this echo is emphasized and its level increases. Consequently, measurement precision of a defect position and thickness can be greatly improved.

Ultrasonic measurement lines in the test object in this time are as shown in FIGS. 11A to 11C. All the measurement lines become ones reflected at the same point R on the bottom surface of the test object. Hence, in this embodiment, thickness of the test object at the point R can be measured accurately. Here, in FIGS. 11A to 11C, T21 (1) shows the center position of the tire 10 at the state 1;

T21 (2) shows the center position of the tire 10 at the state 2;

T21 (3) shows the center position of the tire 10 at the state 3;

T22 (1) shows the center position of the tire 12 at the state 1;

T22 (2) shows the center position of the tire 12 at the state 2;

T22 (3) shows the center position of the tire 12 at the state 3;

L1 shows a ultrasonic wave propagation path at the state 1;

L2 shows a ultrasonic wave propagation path at the state 2;

L3 shows a ultrasonic wave propagation path at the state 3;

"R" shows a ultrasonic wave reflection point on the bottom surface;

"92" shows the top surface of the test object 64;

"94" shows the bottom surface of the test object 64.

Figure 12A:
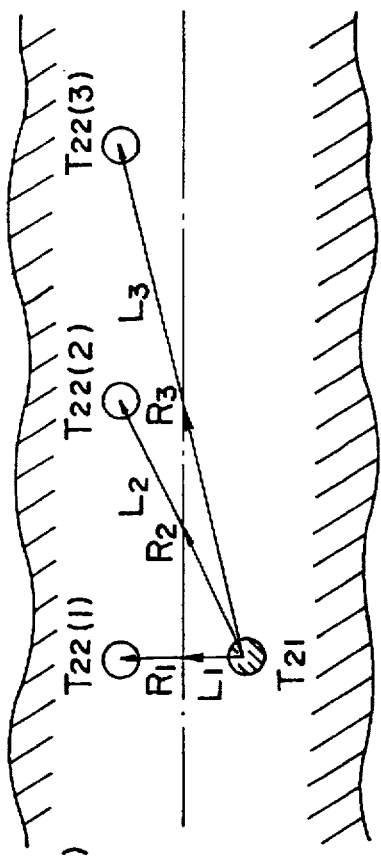
FIGS. 12A to 12C are explanatory diagrams of ultrasonic measurement lines inside a test object according to the first embodiment.
Figure 12B:
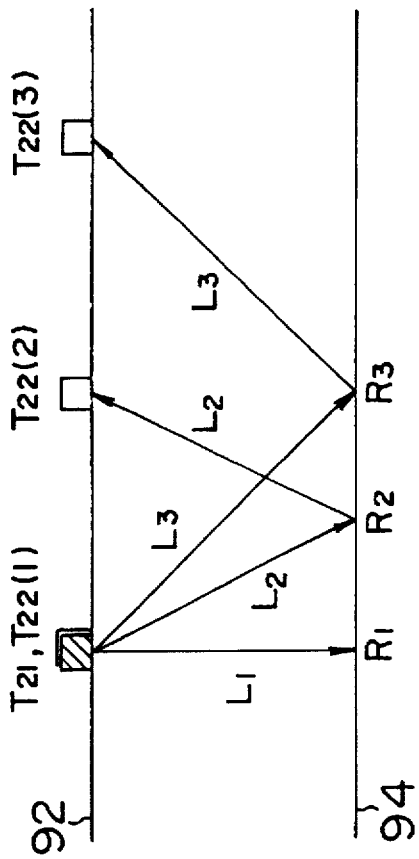
Figure 12C:
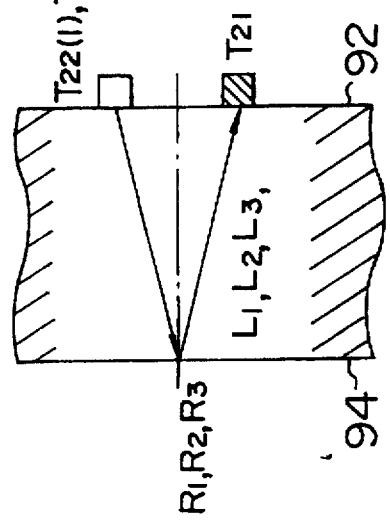

On the other hand, ultrasonic measurement lines in the test object 64 in the first embodiment are as shown in FIGS. 12A to 12C. Following movement of the tires 10 and 12, the ultrasonic wave reflection point moves from R1 to R2 and R3. Therefore, in the first embodiment, only the average thickness of the bottom surface B from R1 to R3 can be measured. Here, in FIGS. 12A to 12C, R1 shows a ultrasonic wave reflection point at the state 1 in FIG. 5;

R2 shows a ultrasonic wave reflection point at the state 2 in FIG. 5;

R3 shows a ultrasonic wave reflection point at the state 3 in FIG. 5.

In the second embodiment, although cross-sectional layer images of the test object 64 cannot be displayed in running because of the movement manner of the tires 10 and 12, this is suitable to accurately measure of thickness at the specific position of the test object 64. Then, a method that, after grasping the outline of the test object 64 in the first embodiment, only particularly necessary positions are precisely measured in the second embodiment can be considered.

Figure 13:
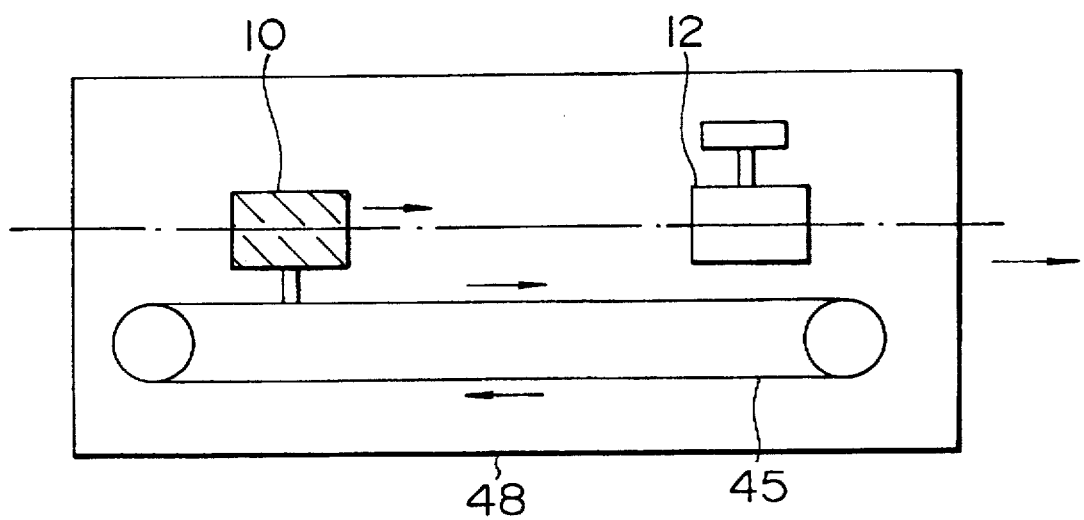
FIG. 13 is an explanatory diagram of the third embodiment of the present invention.

FIG. 13 shows the third embodiment of the present invention, and this is characterized in the arrangement of the tires 10 and 12 on a line along the advancing direction of the frame 48. The tire 12 is mounted to the frame 48 in free rotation, its position is fixed, and rotation of the tire 12 can move the frame 48. On the other hand, the tire 10 is driven with a timing belt and the like, and by rotationally moving, can change its position relative to the frame 48. Therefore, the tires 10 and 12 are on a line, and further, can mutually change their space relatively. In general, a sound field of ultrasonic waves (sound strength distribution) transmitted from and received to a tire probe has a characteristic depending on a radiating direction also in a horizontal plane. Against this, in the third embodiment, since the direction of the waves transmitted from and received to the tire probe for transmission and reception is fixed, this has an advantage that this is not affected by the direction dependency of the tire probe in the horizontal plane.

Figure 14:
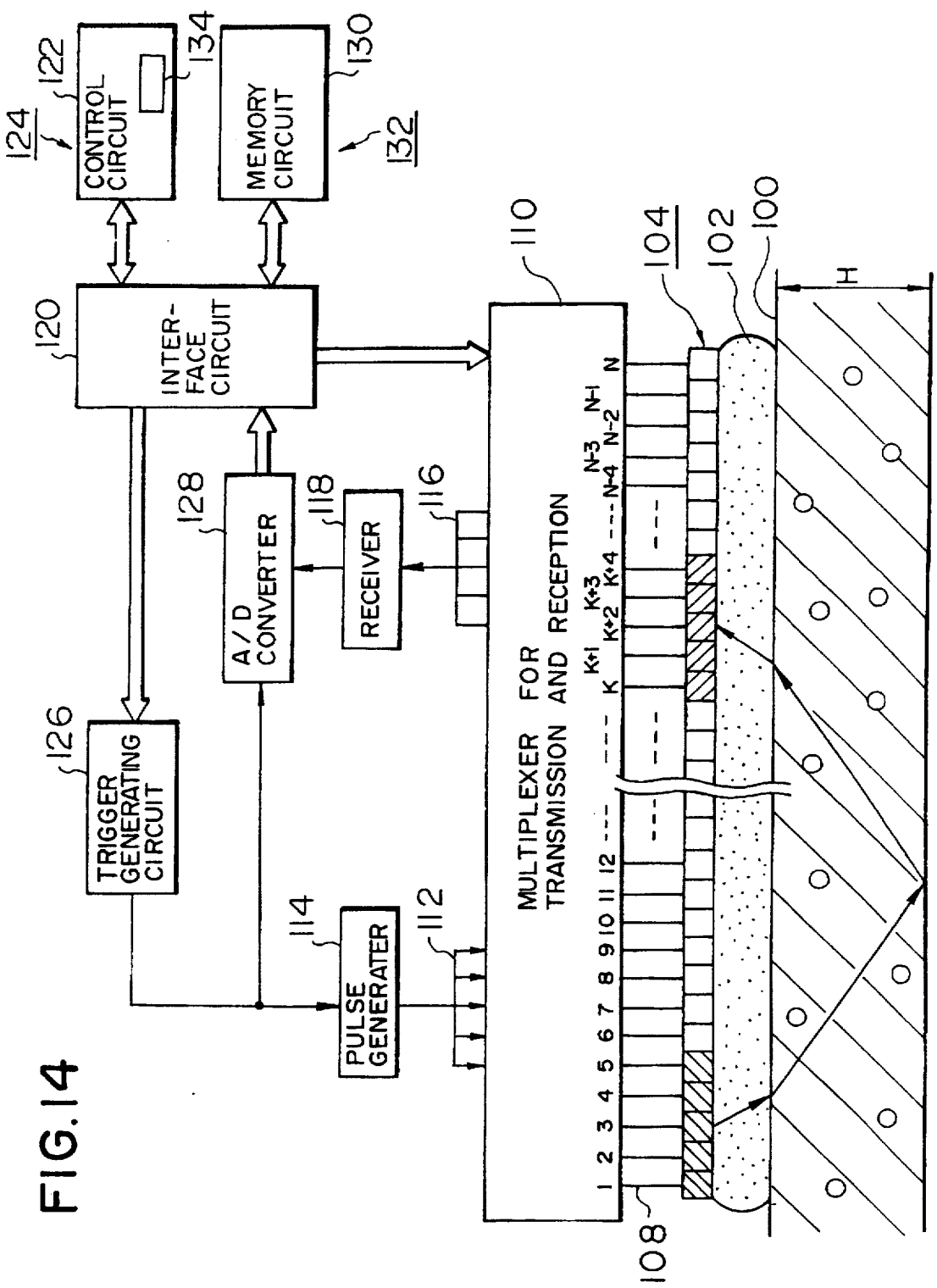
FIG. 14 is a schematic structure and circuit block diagram of the fourth embodiment of the present invention.
Figure 15:
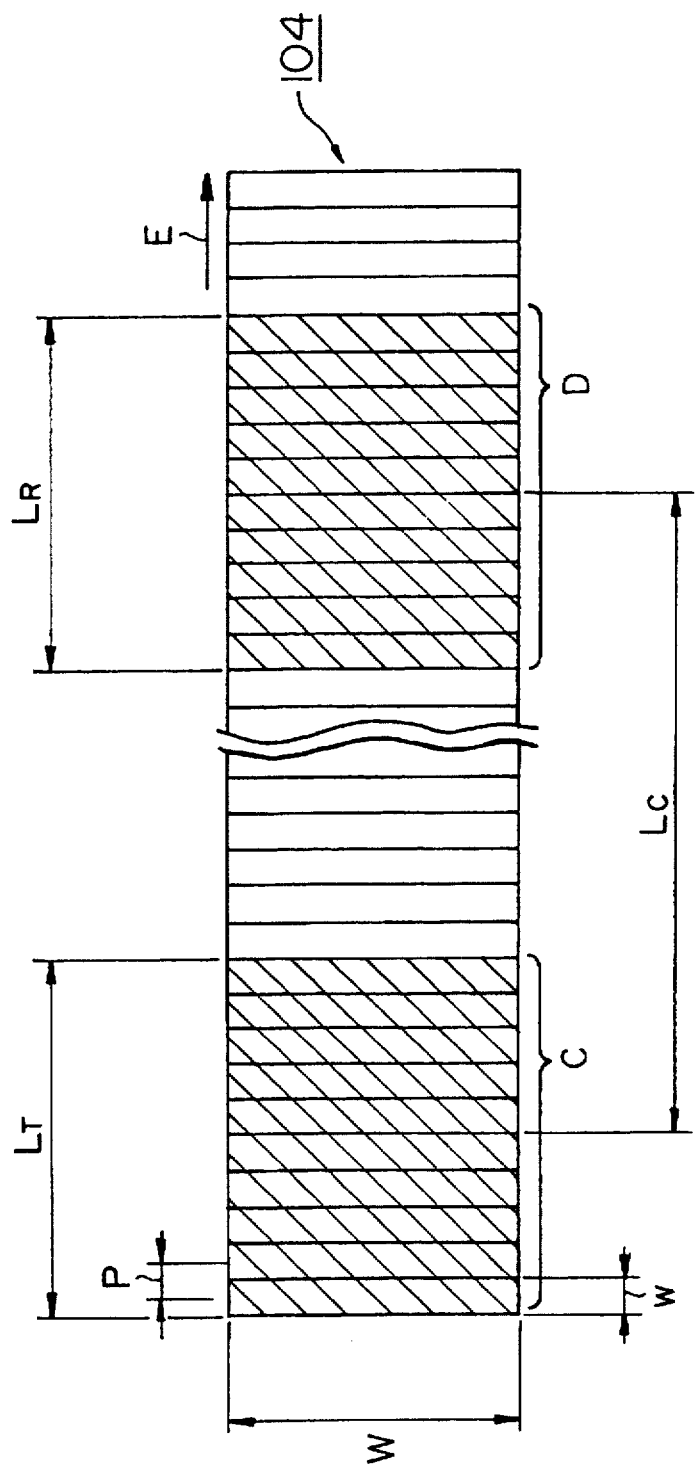
FIG. 15 is an explanatory diagram of an array type of ultrasonic oscillator used in the fourth embodiment.

FIG. 14 and FIG. 15 show the fourth embodiment of the present invention. FIG. 14 shows an entire structure of an apparatus according to the present invention for detecting flaws using supersonic waves, and FIG. 15 shows an array type of ultrasonic oscillator used in the fourth embodiment. In this fourth embodiment, especially in the case not requiring a cross-sectional layer image of the test object, the configuration and operations of an apparatus for detecting flaws using supersonic waves for attaining the objects of the present invention will be described.

In FIG. 14, an array type of ultrasonic oscillator 104 is located on a surface of a test object 100 through an acoustic connection medium 102 such as water, jelly, gel, oil and the like. The array type of ultrasonic oscillator 104 is composed of N pieces of ultrasonic oscillators, i.e., element oscillators. The n pieces of element oscillators from the first element oscillator to the nth one are used for transmission, and n pieces of element oscillators, for example, from the kth element oscillator to the (k+n−1)th one are used for reception.

The array type of ultrasonic oscillator 104, as shown in FIG. 15, is composed of N pieces of rectangular element oscillators, one of which has an element width w and a length (width of the oscillator) W, at a pitch p in a line arrangement. Here, "C" shows an ultrasonic oscillator for transmission, "D" shows a ultrasonic oscillator for reception, $L_C$ shows a center-to-center distance between ultrasonic oscillators for transmission and reception,, $L_T$ shows a length of the ultrasonic oscillator for transmission C, $L_R$ shows a length of the ultrasonic oscillator for reception D, and "E" shows the scanning direction of the ultrasonic oscillator for reception D. Therefore, if the ultrasonic oscillator for reception D is scanned along the scanning direction E one by one, the center-to-center distance $L_C$ between ultrasonic oscillators for transmission and reception changes by the pitch p.

Each element oscillator of the array type of ultrasonic oscillator 104 is connected to a multiplexer for transmission and reception 110 respectively through signal lines 108. The multiplexer for transmission and reception 110 is connected to a pulse generator 114 through reception terminals 112. Further, the multiplexer for transmission and reception 110 is also connected to a receiver 118 through reception terminals 116. Furthermore, the multiplexer for transmission and reception 110 is connected to a control circuit 122 through an interface circuit 120, and has switching control performed by the control circuit 122. The interface circuit 120 and control circuit 122, as a whole, compose a switching control means 124.

Based on a trigger signal generated in the trigger generating circuit 126 through the interface circuit 120 with a command from the control circuit 122, the pulse generator 114 drives the element oscillators for transmission designated with the multiplexer for transmission and reception 110. If, by the multiplexer for transmission and reception 110, the element oscillators for reception are designated, the element oscillators for transmission generate pulsed ultrasonic waves, and propagate the ultrasonic waves into the test object 100 through acoustic connection medium 102. The ultrasonic waves propagated inside the test object 100 arrive at the element oscillators for reception, and are received.

After the received reception waveform data are amplified to the predetermined level in the receiver 118, they are converted to digital signals in an A/D converter 128 in the timing based on a trigger signal generated in the trigger generating circuit 126, and are stored in a memory circuit 130 through the interface circuit 120. The pulse generator 114, trigger generating circuit 126, receiver 118, A/D converter 128, interface circuit 120, memory circuit 130, and control circuit 122, as a whole, compose a reception data acquisition memory means 132 for acquiring and storing reception waveform data from the array type of ultrasonic oscillators 104 at a plurality of positions.

Since the control circuit 122 has a function as an adding means 134, this adds each obtained reception waveform data per corresponding time. If the control circuit 122 adds each reception waveform data per corresponding time with the adding means 134, the level of the surface wave component is lowered due to a phase cancellation effect derived from their different arrival times, while the level of the target echoes or the bottom echoes increases due to emphasis by addition because of little change of their arrival times.

Next, operations of the fourth embodiment will be described. The multiplexer for transmission and reception 110 connects the pulse generator 114 to n pieces of element oscillators from the first element oscillator to the nth one through the transmission terminals 112 with a command from the control circuit 122. Similarly, the multiplexer for transmission and reception 110 connects the receiver 118 to n pieces of element oscillators from the kth element oscillator to the (k+n−1)th one through the reception terminals 116 with a command from the control circuit 122. The pulse generator 114 is always connected to the n pieces of element oscillators from the first element oscillator to the nth one. The receiver 118 is connected to n pieces of element oscillators, for example, from the (n+1)th element oscillator to the 2nth one in measurement start timing. At this time, if the trigger generating circuit 126 generates a trigger signal after reception of a command from the control circuit 122 through the interface circuit 120, the pulse generator 114 drives n pieces of element oscillators from the first element oscillator to the nth one on the basis of this trigger signal, and radiates ultrasonic waves into the test object 100.

The ultrasonic waves propagated inside the test object 100 arrive at the n pieces of element oscillators from the (n+1)th element oscillator to the 2nth one, and are received. After the received reception waveform signals are amplified to the predetermined level with the receiver 118, they are converted to digital signals in the A/D converter 128 in the timing based on a trigger signal generated in the trigger generating circuit 126, and are stored in the memory circuit 130. The reception waveform data received at this time are the waveform data interfered with surface waves and target echoes inside the test object or bottom echoes, similarly to the conventional reception waveform data in FIG. 3. After the reception waveform data are stored in the memory circuit 130, the multiplexer for transmission and reception 110 connects the receiver 118 to n pieces of element oscillators from the (n+2)th element oscillator to the (2n+1)th one through the reception terminals 116 with a command from the control circuit 122. Further, by the same manner, the received waveforms are converted to digital signals, and are stored in the memory circuit 130. Furthermore, this apparatus shifts n pieces of element oscillators for reception one-by-one with electronic scanning, and repeats this processing until the nth element oscillator becomes the Nth element oscillator. If this apparatus shifts n pieces of element oscillators for reception one-by-one with this scanning, the center-to-center distance $L_C$ between the element oscillators for transmission and reception changes by the pitch p. Therefore, if, using the adding means 134 of the control circuit 122, this apparatus adds each obtained reception waveform data per corresponding time, because of the same principle as that of the first embodiment, the level of the surface wave component is lowered due to a phase cancellation effect derived from their different arrival times, while the level of the target echoes or the bottom echoes increases due to emphasis by addition because of little change of their arrival times. Thus, waveform data composed of depressed surface waves, and emphasized target echoes or bottom echoes can be obtained.

In this fourth embodiment, similarly to the first embodiment, ultrasonic measurement lines inside the test object 100 are shown in FIGS. 12A to FIG. 12C. Thus, as this apparatus shifts the element oscillators for reception on-by-one with the electronic scanning, the reflection point moves from R1 to R2 and further R3. Therefore, in the third embodiment, only average the thickness of the bottom surface B of the test object 106 from R1 to R3 can be measured.

Figure 16:
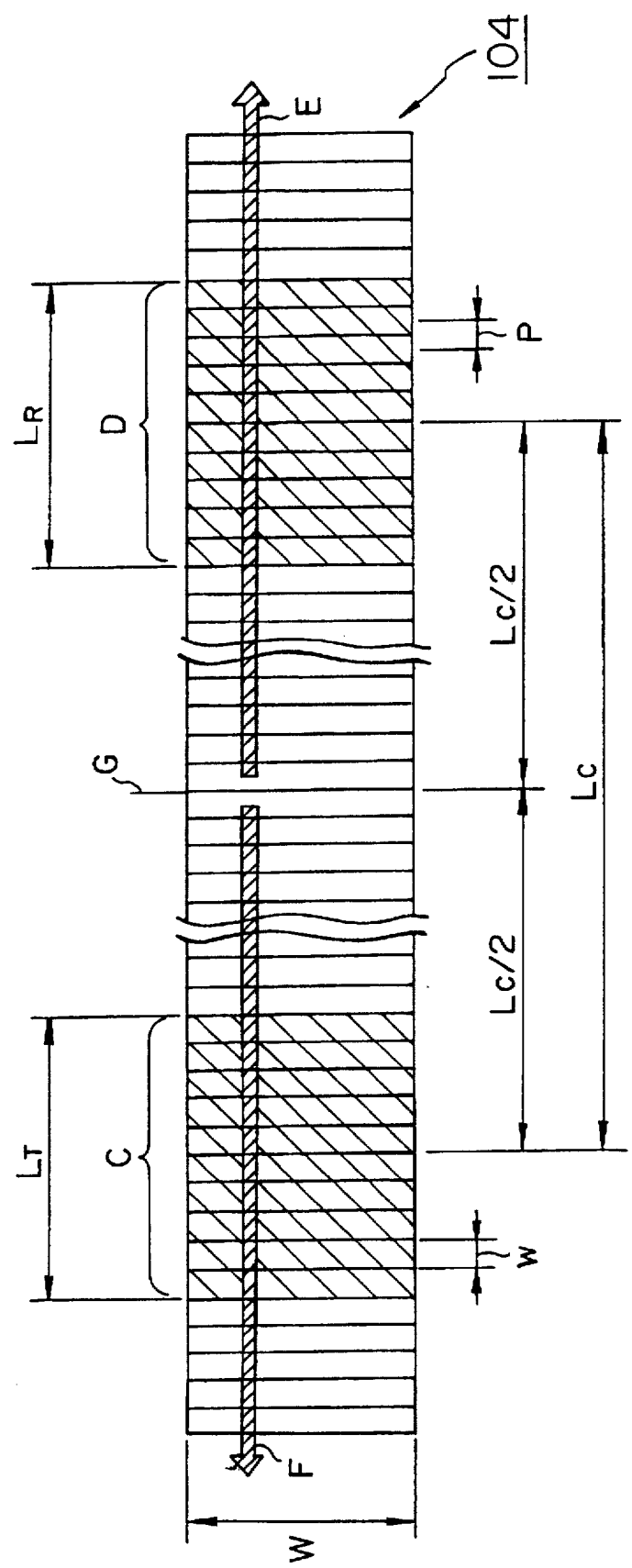
FIG. 16 is an explanatory diagram of an array type of ultrasonic oscillator used in the fifth embodiment of the present invention.

Subsequently, FIG. 16 shows an array type of ultrasonic oscillator 104 used in the fifth embodiment of the present invention. Although the fifth embodiment can be realized with the same apparatus as that of the fourth embodiment according to the present invention, the electronic scanning manner of the element oscillator for transmission is different from that of the element oscillator for reception.

In the fifth embodiment, as shown in FIG. 16, at measurement start, this apparatus uses n pieces of element oscillators from the {(N/2)−n+1} element oscillator to the (N/2)th one as a ultrasonic oscillator for transmission on the basis of its center (the center line G of oscillators in FIG. 16). In addition, this uses n pieces of element oscillators from the {(N/2)+1}th element oscillator to the {(N/2)+n}th one as an oscillator for reception. Still more, as the measurement processing advances, this controls to switch each element used for transmission and each element for reception in a mirror image on the basis of its center in shifting one-by-one with electronic scanning. Here, "F" shows the scanning direction of the ultrasonic oscillator for transmission C, and "E" shows the scanning direction of the ultrasonic oscillator for reception D.

If, using the adding means 134 provided in the control circuit 122 in FIG. 14, this apparatus adds each obtained reception waveform data per corresponding time, because of the same principle as that of the fourth embodiment, the level of the surface wave component is lowered due to a phase cancellation effect derived from their different arrival times, while the level of the target echoes or the bottom echoes increases due to emphasis by addition because of little change of their arrival times. Thus, waveform data composed of depressed surface waves, and emphasized target echoes or bottom echoes can be obtained. Ultrasonic measurement lines in the test object 106 in this time are as shown in FIGS. 11A to 11C. All the measurement lines become ones reflected at the same point R on the bottom surface of the test object 100. Hence, in this embodiment, the thickness of the test object 100 at the point R can be measured accurately. Consequently, the fifth embodiment can measure the thickness of the specific position on the test object 100 in precision higher than the fourth embodiment.

Figure 17:
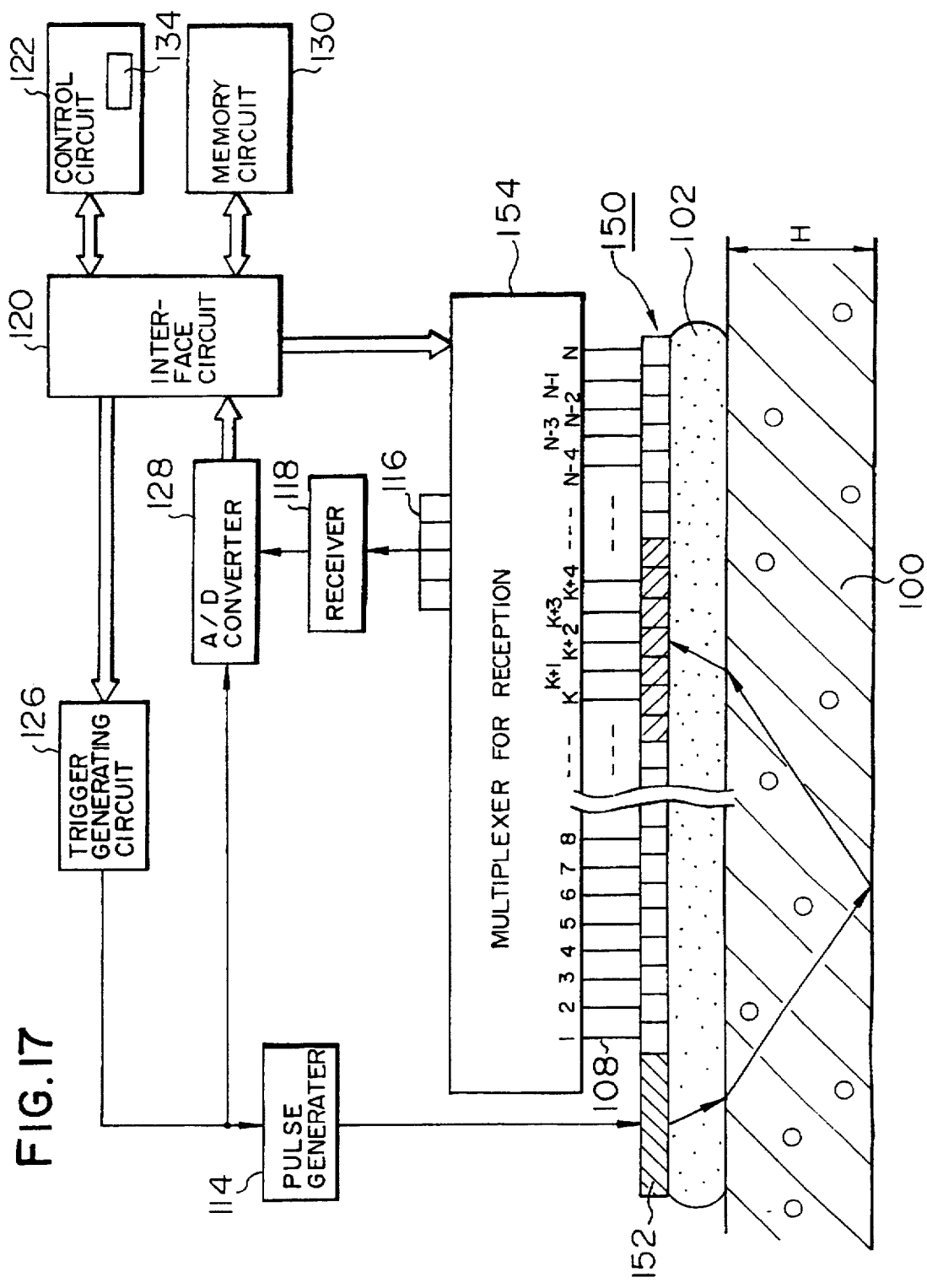
FIG. 17 is a schematic structure and circuit block diagram of the sixth embodiment of the present invention.
Figure 18:
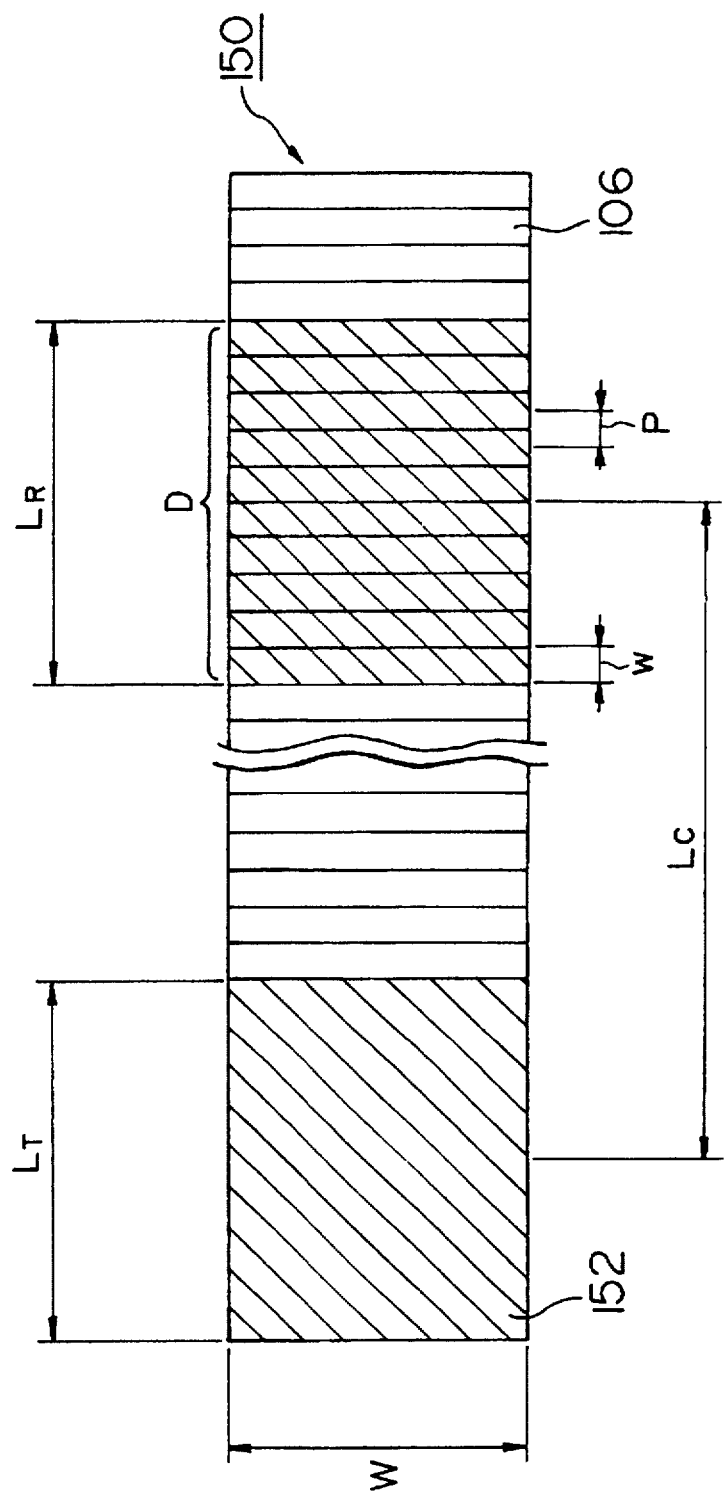
FIG. 18 is an explanatory diagram of an array type of ultrasonic oscillator used in the sixth embodiment of the present invention.
Figure 19:
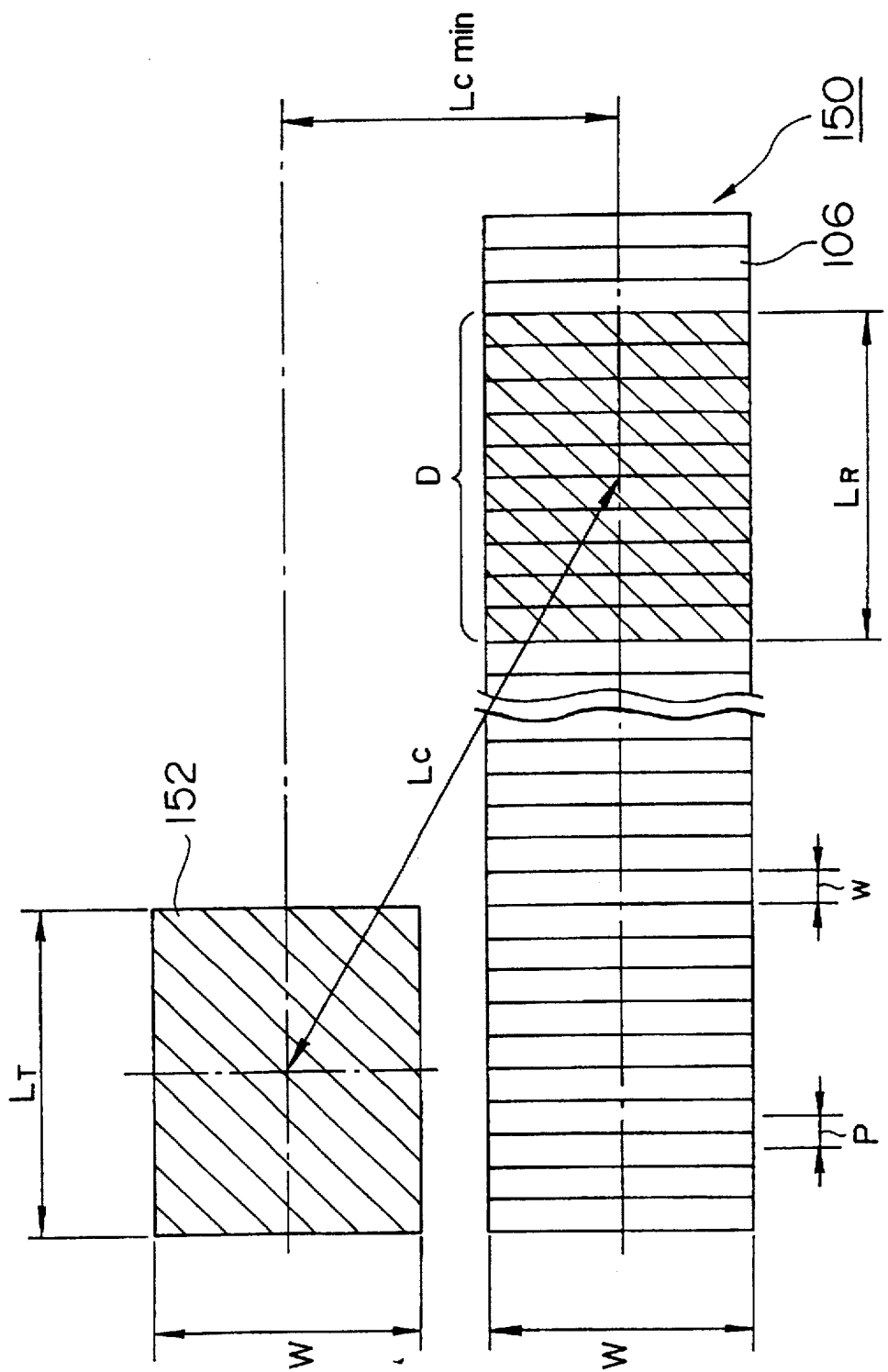
FIG. 19 is an explanatory diagram of another array type of ultrasonic oscillator.

Subsequently, FIG. 17 to FIG. 19 show the sixth embodiment of the present invention. FIG. 17 shows an entire structure of an apparatus according to the sixth embodiment for detecting flaws using supersonic waves. FIG. 18 shows an array type of ultrasonic oscillator, and FIG. 19 shows a modified example of an array type of ultrasonic oscillator used in the sixth embodiment.

In FIG. 17, an array type of ultrasonic oscillator 150 is located on a surface of a test object 100 through acoustic connection medium 102. This array type of ultrasonic oscillator 150 replaces n pieces of element oscillator from the first element oscillator to the nth one, to a single ultrasonic oscillator for transmission 152 having a predetermined area, and uses residual element oscillators as oscillators for reception. The residual element oscillators for reception are connected through signal lines 108 to a multiplexer for reception 154 being a switching means. The multiplexer for reception 154 is connected to a receiver 118 through reception terminals 116. The ultrasonic oscillator for transmission 152 is directly driven with a pulse generate 114.

At the ultrasonic oscillator for transmission 150 in FIG. 18 and FIG. 19, the center-to-center distance $L_C$ between the ultrasonic oscillator 152 composed of, for example, element oscillators from the kth element oscillator to the (k+4)th one and the ultrasonic oscillator for reception D changes by the pitch p, if the element oscillators of the ultrasonic oscillator for reception D are shifted one-by-one. Here, $L_{C\ min}$ in FIG. 19 shows the shortest center-to-center distance between the ultrasonic oscillators for transmission and reception. And, the sixth embodiment can obtain the same effect as the fourth embodiment.

Figure 20:
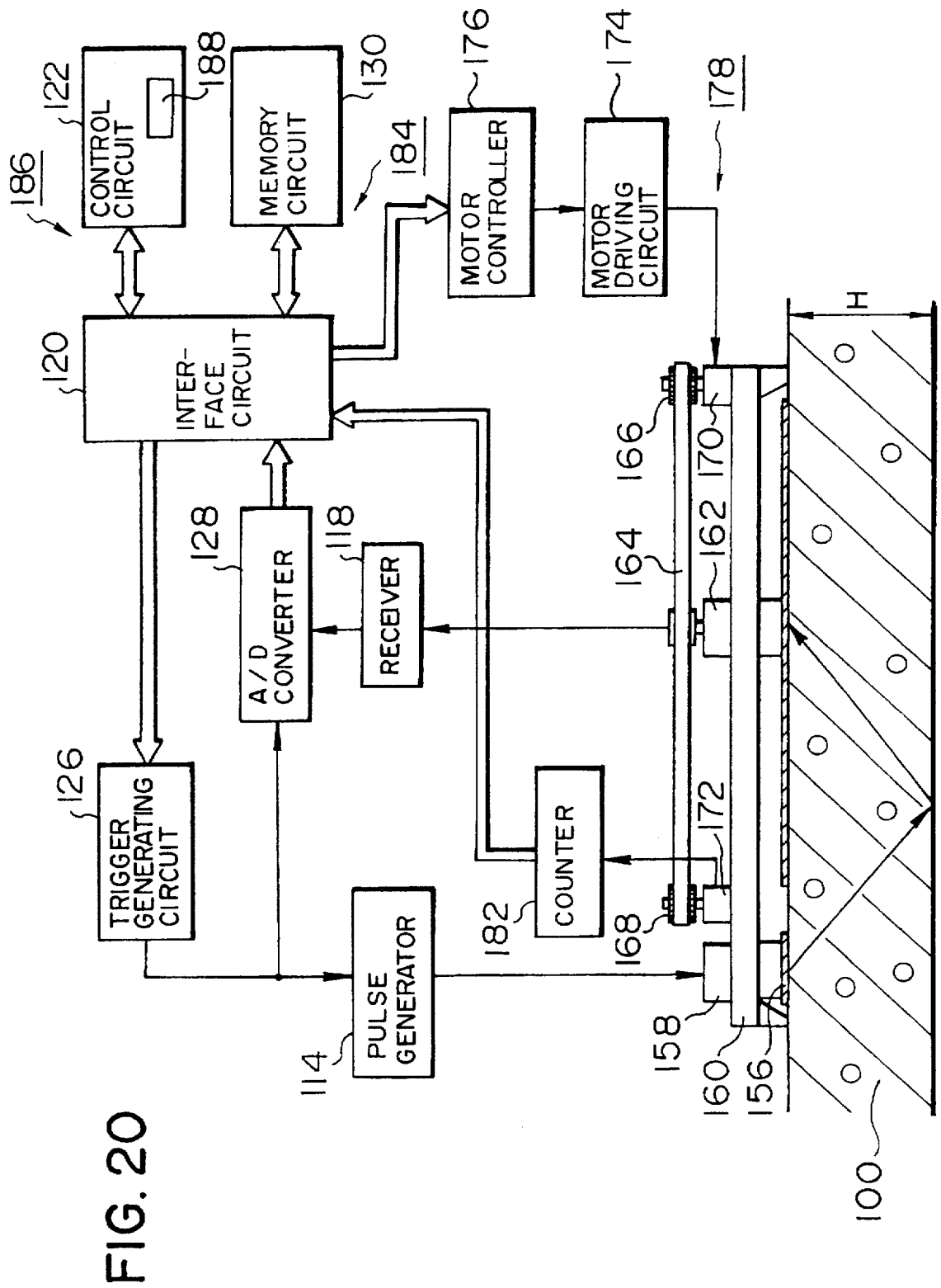
FIG. 20 is a schematic structure and circuit block diagram of the seventh embodiment of the present invention.

FIG. 20 shows an apparatus according to the seventh embodiment for detecting flaws using supersonic waves. The seventh embodiment is also an example of the case not especially requiring a cross-sectional layer image of the test object. One ultrasonic probe 158, for example, a ultrasonic probe for transmission is fixed on the test object 100 through an acoustic connection medium 156. Thus, one ultrasonic probe 158 is fixed on a frame 160, and is fixed at the optional position to be desired to measure, on the test object 100. The other ultrasonic probe 162, for example, an ultrasonic probe for reception, is connected to a belt 164. The belt 164 is wrapped between driving gears 166 and 168, the driving gear 166 is connected to a stepping motor 170, and the driving gear 168 is connected to a rotary encoder 172. The stepping motor 170 is driven a motor driving circuit 174, and the motor driving circuit 174 is controlled by a motor controller 176. The belt 164, driving gears 166 and 168, stepping motor 170, motor driving circuit 174 and motor controller 176, as a whole, compose a driving means 178. The ultrasonic probe 162 can move on the frame 160 with the driving means 178. Thus, the ultrasonic probe 162 contacts to the surface of the test object 100 through an acoustic medium 180, and can move on a definite range of the test object 100 that is limited with a frame 160. In other words, since the stepping motor 170 can rotate and stop with a command from the control circuit 122 through the interface circuit 120, motor controller 176 and motor driving circuit 174, this can brake and stop the ultrasonic probe 162 connected to the belt 164 at the designated position, and can move it to the designated position.

In addition, the control circuit 122 can recognize a position of the ultrasonic probe 162 on the frame 160, that is, a position of the ultrasonic probe 162 on the test object 100 with a rotary encoder 172 and a counter 182. The rotary encoder 172 analyzes rotation of the driving gear 168, the counter 182 counts an output of the rotary encoder 172, and outputs to the control circuit 122 through the interface circuit 120. The control circuit 122, based on the output of the counter 182, recognizes a position of the frame 160 of the ultrasonic probe 162 on the test object 100, controls the driving means 178, and controls braking, stopping and moving of the ultrasonic probe 162. Therefore, the rotary encoder 172, counter 182, interface circuit 120, and control circuit 122, as a whole, compose a control means 184 for controlling the driving means 178.

The ultrasonic probe 158 is driven with a pulse signal generated in a pulse generator 114, i.e., a pulse generating circuit, the pulse generator 114 outputs a pulse signal through the interface circuit 120 with a trigger signal generated in the trigger generating circuit 126 with a command from the control circuit 122. Utltrasonic waves radiated from the ultrasonic probe 158 propagate into the test object 100 through the acoustic medium 156, arrive at the ultrasonic probe 162 through the acoustic medium 180, and are received. After the received waveform signals are amplified to the predetermined level with the receiver 118, they are converted to digital signals in the A/D converter 128 in the timing based on a trigger signal generated in the trigger generating circuit 126, and are stored in the memory circuit 130. Therefore, the pulse generator 114, trigger generating circuit 126, receiver 118, A/D converter 128, memory circuit 130, interface circuit 120, and control circuit 122, as a whole, compose a reception data acquisition memory means 186 for acquiring and storing ultrasonic reception waveform data at a plurality of positions on the frame 160.

In addition, since the control circuit 122 has a function as an adding means 188, this adds each obtained reception waveform data per corresponding time. If the control circuit 122 adds each reception waveform data per corresponding time with the adding means 188, the level of the-surface wave component is lowered due to phase cancellation effect derived from their different arrival times, while the level of the target echoes or the bottom echoes increases due to emphasis by addition because of little change of their arrival times. Thus, waveform data composed of depressed surface waves, and emphasized target echoes or bottom echoes can be obtained. Hence, using the seventh embodiment, similarly to the above-mentioned embodiments, changing a position of the ultrasonic probe 158 relative to that of the ultrasonic probe 162, acquiring ultrasonic reception waveforms at a plurality of predetermined positions on the way of changing, and adding these waveforms per corresponding time, a level of a surface wave component, which becomes an interfering wave, is depressed, but a level of a target echo or a bottom echo is emphasized through addition and its level increases. Thus, waveform data composed of depressed surface waves, and emphasized target echoes or bottom echoes can be obtained, and hence, measurement precision of inside defect positions and the thickness can be greatly improved.

FIG. 21 shows an apparatus according to the eighth embodiment of the present invention for detecting flaws using supersonic waves. This eighth embodiment is also an example of the case not especially requiring a cross-sectional layer image of the test object. Although, in the seventh embodiment, ultrasonic probe is fixed and the other ultrasonic probe moves, the eighth embodiment changes the relative distance between both ultrasonic probes through moving both ultrasonic probes.

In FIG. 21, one ultrasonic probe, for example, a ultrasonic probe for transmission 200 is located on the test object 100 through the acoustic connection medium 156. The ultrasonic probe 200 is connected to a belt 202. The belt 202 is wrapped between driving gears 204 and 206, the driving gear 204 is connected to a stepping motor 208, and the driving gear 206 is connected to a rotary encoder 210. The stepping motor 204 is driven by a motor driving circuit 212, and the motor driving circuit 212 is controlled by a motor controller 214. The belt 202, driving gears 204 and 206, stepping motor 204, motor driving circuit 212 and motor controller 214, as a whole, compose a driving means 216.

The ultrasonic probe 200 can move on the frame 218 with the driving means 216. Thus, the ultrasonic probe 200 contacts to the surface of the test object 100 through an acoustic medium 156, and can move on a definite range of the test object 100 that is limited with a frame 218. In other words, the stepping motor 204 can rotate and stop with a command from the control circuit 186 through the interface circuit 120, motor controller 214 and motor driving circuit 212. Therefore, this can brake and stop the ultrasonic probe 200 connected to the belt 202 at the designated position, and can move it to the designated position.

In addition, the control circuit 186 can recognize a position of the ultrasonic probe 200 on the frame 218, that is, a position of the ultrasonic probe 200 on the test object 100 with a rotary encoder 210 and a counter 220. The rotary encoder 210 analyzes rotation of the driving gear 206. The counter 220 counts an output of the rotary encoder 210, and outputs to the control circuit 186 through the interface circuit 120. The control circuit 186, based on the output of the counter 220, recognizes a position of the ultrasonic probe 200 on the frame 218, i.e., a position on the test object 100, controls the driving means 216, and controls braking, stopping and moving of the ultrasonic probe 200. Therefore, the rotary encoder 210, counter 220, interface circuit 120, and control circuit 186, as a whole, compose a control means 222 for controlling the driving means 216. In this manner, in the eighth embodiment, one ultrasonic probe 200 and the other ultrasonic probe 162 can move on the frame 218, and can obtain similar measurement results to the seventh embodiment through changing the relative distance between the ultrasonic probes 200 and 162.

In this manner, changing a position of one ultrasonic probe or one tire probe relative to that of the other ultrasonic probe or the other tire probe, acquiring ultrasonic reception waveforms at a plurality of predetermined positions, and adding these waveforms per corresponding time, a level of a surface wave component becomes low by a phase canceling effect because of different arrival times. However, since the arrival times of the target echo or the bottom echo scarcely changes, this echo is emphasized and its level increases. Consequently, measurement of a defect position and thickness of the test object can be performed in high precision without interference of surface waves.

In case, after initially setting a distance between a pair of ultrasonic probes or tire probes at a predetermined value through locating the pair of ultrasonic probes or tire probes at optionally designated positions on a test object, this apparatus controls, on the basis of the initial set positions, the pair in order that the pair are located in definite but opposite directions in the same distance on a test object, this can measure thickness at the specific position of the test object more accurately than the others, although this cannot detect cross-sectional layer images of the test object.

Further, the present invention is not limited by the numbers shown in embodiments.

What is claimed is:

1. A flaw detection apparatus, comprising:

a tire probe comprising a frame, and a pair of tires each having an ultrasonic oscillator for transmission or reception of ultrasonic waves, said pair of tires arranged on a line along an advancing direction of said frame, and a driving means for moving said frame on a test object through rotationally driving a first tire of said pair of tires and for moving a second tire of said pair of tires relative to the frame through rotationally driving said second tire of said pair of tires;

a control means for controlling said driving means to move said tire probe on the test object through rotationally driving said first tire of said pair of tires while changing a distance between said pair of tires through rotationally driving said second tire of said pair of tires;

a reception data acquisition memory means for acquiring and storing waveform data of ultrasonic reception signals at each of a plurality of predetermined positions during the rotational driving of said pair of tires; and an adding means for adding each waveform data acquired with said reception data acquisition memory means at the plurality of predetermined positions.

* * * * *